(12) United States Patent
Hochberg et al.

(10) Patent No.: US 6,306,833 B1
(45) Date of Patent: *Oct. 23, 2001

(54) METHODS AND COMPOSITIONS FOR INDUCING TUMOR-SPECIFIC CYTOTOXICITY

(75) Inventors: Abraham Hochberg; Suhail Ayesh, both of Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/568,059

(22) Filed: May 10, 2000

Related U.S. Application Data

(60) Division of application No. 09/165,240, filed on Oct. 1, 1998, now Pat. No. 6,087,164, which is a continuation-in-part of application No. 08/943,608, filed on Oct. 3, 1997, now abandoned.

(51) Int. Cl.[7] .......................... A01N 43/04; A61K 31/70; C12Q 1/68; C12N 15/00; C12N 5/00
(52) U.S. Cl. ............................... 514/44; 435/6; 435/69.1; 435/320.1; 435/325; 435/375
(58) Field of Search .......................... 514/44; 435/320.1, 435/6, 69.1, 325, 375; 536/23.1, 24.5

(56) References Cited

FOREIGN PATENT DOCUMENTS

| | | |
|---|---|---|
| 2725213 | 4/1996 | (FR) . |
| 714867 | 4/1996 | (AU) . |
| WO 94/13824 | 6/1994 | (WO) . |
| WO 95/05835 | 3/1995 | (WO) . |
| WO 95/24503 | 9/1995 | (WO) . |
| WO 96/05321 | 2/1996 | (WO) . |

OTHER PUBLICATIONS

Orkin et al. Report and recommendations of the panel to assess the NIH investment in research on gene therapy, pp. 1–23, Dec. 1995.*
W. French Anderson, Human gene therapy, Nature, vol. 392, Supp., pp. 25–30, Apr. 1998.*
Marshall et al. Science, vol. 269, pp. 1050–1055, Aug. 1995.*
Gómez–Navarro et al. European Journal of Cancer, vol. 35, No. 6, pp. 867–885 (1999).*
Anderson, 1998, "Human gene therapy", Nature 392:25–30.
Ariel et al. 1997, "The product of the imprinted H19 gene is an oncofetal RNA", J. Clin. Pathol. Mol. Pathol. 50:34–44.
Branch, 1998, "A Good antisense molecule is hard to find", TIBS 23:45–50.
Brannan et al., 1990, "The product of the H19 gene may function as an RNA", Mol. Cell. Biol. 10:28–36.
Brunkow and Tilghman, 1991, "Ectopic expression of the H19 gene in mice causes prenatal lethality", Genes & Dev. 5:1092–1101.
Crooke, 1998, "Basic principles of antisense therapeutics", in: *Antisense Research and Application*, Crooke, ed., Springer–Verlag, pp. 1–50.
Crooke et al., 1997, "A roundtable on the state of the industry", Nature Biotechnol. 15:522.
Davis et al., 1987, "Expression of a single transfected cDNA converts fibroblasts to myoblasts", Cell 51:987–1000.
DeGroot et al., 1994, "Genetic imprinting in human embryogenesis H19 and IGF2 gene expression", Trophoblast Res. 8:285–302.
Elkin et al., 1995, "The expression of the imprinted H19 and IGF–2 genes in human bladder carcinoma", FEBS Lett. 374:57–61.
Glassman et al., 1996, "Relaxation of imprinting in carcinogenesis", Cancer Genet. Cytogenet. 89:69–73.
Gura, 1995, "Antisense has growing pains", Science 270:575–577.
Hao et al., 1993, "Tumour–suppressor activity of H19 RNA", Nature 365:764–767.
Holthuizen et al., 1993 "Transcriptional regulation of the major promoters of the human IGF–II gene", Mol. Reprod. Dev. 35:391–393.
Hu et al., 1997 "Genomic deletion of an imprint maintenance element abolishes imprinting of both insulin–like growth factor II and H19", J. Biol. Chem. 272:20715–20720.
Huber et al., 1991, "Retroviral–mediated gene therapy for the treatment of hepatocellular carcinoma: an innovative approach for cancer therapy", Proc. Natl. Acad. Sci. USA 88:8039–8043.
Hurst et al., 1996, "Imprinted genes have few and small introns", Nature Genetics 12:234–237.
Kaneko et al. 1995, "Adenovirus–mediated gene therapy of hepatocellular carcinoma using cancer–specific gene expression", Cancer Res. 55:5283–5287.
Leighton et al., 1995, "Disruption of imprinting caused by deletion of the *H19* gene region in mice", Nature 375:34–39.

(List continued on next page.)

*Primary Examiner*—Sean McGarry
*Assistant Examiner*—Janet Epps
(74) *Attorney, Agent, or Firm*—Pennie & Edmonds LLP

(57) ABSTRACT

The invention relates to the specific expression of heterologous sequences, particularly genes encoding cytotoxic products, in tumor cells under the control of regulatory transcriptional sequences. Particularly preferred promoters include H19 regulatory sequences, the IGF-1 promoter and the IGF-2 P3 and P4 promoters. The invention provides expression constructs and methods of administering such expression constructs. The compositions and methods of the invention are useful in the treatment of cancer.

12 Claims, 15 Drawing Sheets

OTHER PUBLICATIONS

Figure 2:
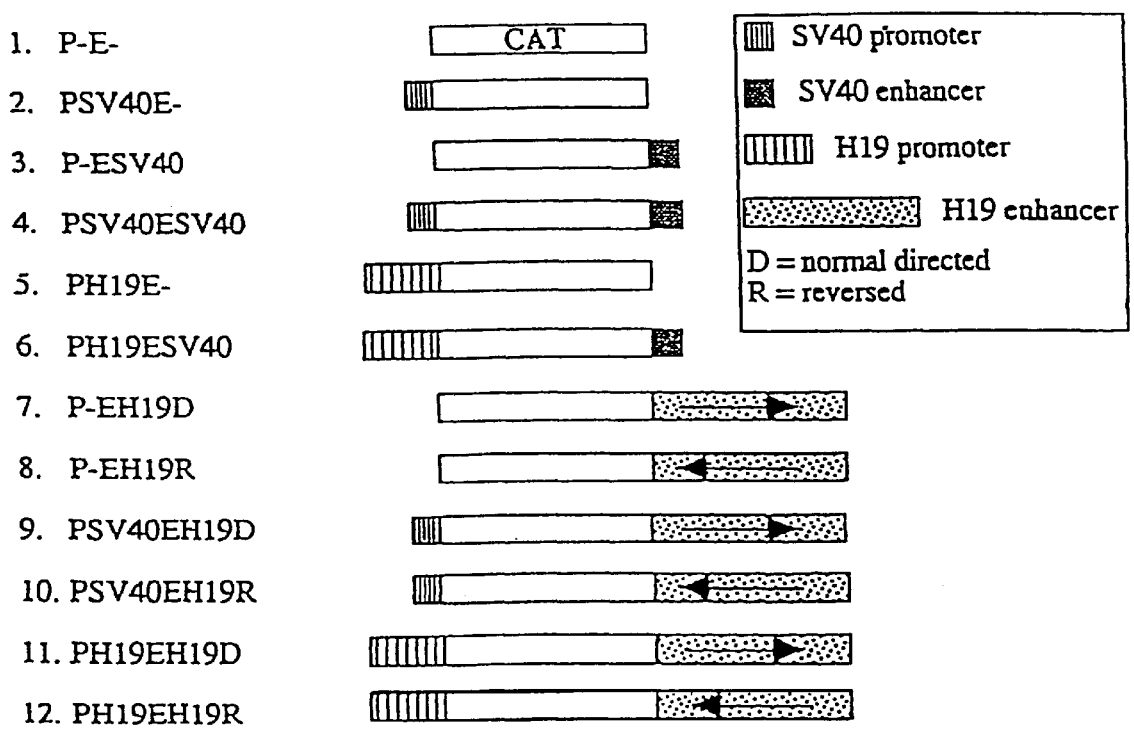

Lustig–Yariv et al., 1997, "The expression of the imprinted genes H19 and IGF–2 in cholriocarcinoma cell lines. Is h19 a tumor suppressor gene?", Oncogene 15:169–177.

Ogawa et al., 1993, "Relaxation of insulin–like growth factor II gene imprinting implicated in Wilms' tumour", Nature 362:747–749.

Orkin et al., 1995, "Report and recommendations of the panel to assess the NIH investment in research on gene therapy", pp. 1–23.

Osaki et al., 1994, "Gene therapy for carcinoembryonic antigen–producing human lung cancer cells by cell type–specific expression of herpes simplex virus thymidine kinase gene", Cancer Res. 54:5258–5261.

Pachnis et al., 1984, "Locus unlinked to a α–fetoprotein under the control of the murine raf and Rif genes", Proc. Natl. Acad. Sci. USA 81:5523–5527.

Pfeiffer et al., 1996, "The structural H19 gene Is required for transgene imprinting", Proc. Natl. Acad. Sci. USA 93:13876–13883.

Poirier et al., 1991, "The murine H19 gene is activated during embryonic stem cell differentiation in vitro and at the time of implantation in the developing embryo", Devel. 113:1105–1114.

Rachmilewitz et al., 1992, "Transcription of the H19 gene in differentiating cytotrophoblasts from human placenta", Mol. Reprod. Dev. 32:196–202.

Rainier et al., 1993, "Relaxation of imprinted genes in human cancer", Nature 362:747–749.

Seo et al., 1998, "Different protein–binding patterns in P3 promoter region of the human insulin–like growth factor II gene in the human liver cirrhosis and hepatocellular carcinoma tissues", J. Korean Med. Sci. 13:171–178.

Vile et al., 1993, "Use of tissue–specific expression of the herpes simplex virus thymidine kinase gene to inhibit growth of established murine melanomas following direct intratumoral injection of DNA", Cancer Res. 53:3860–3864.

Wilkins, 1988, "Genomic imprinting and carcinogenesis", Lancet, Feb. 13;1(8581):329–31.

Kaneko et al. 1995, "Adenovirus–mediated gene therapy of hepatocellular carcinoma using cancer–specific gene expression", Cancer Res. 55:5283–5287.

Xu et al., 1996, "Tissue specific growth suppression and chemosensitivity promotion in human hepatocellular carcinoma cells by retroviral–mediated transfer of the wild–type p53 gene", Hepatol. 24:1264–1268.

* cited by examiner

```
     CTGCAGGGCCCCAACAACCCTCACCAAAGGCCAAGGTGGTGACCGACGGACCCACAGCGG
  1  ---------+---------+---------+---------+---------+---------+ 60
     GACGTCCCGGGGTTGTTGGGAGTGGTTTCCGGTTCCACCACTGGCTGCCTGGGTGTCGCC
     |
  -837

GGTGGCTGGGGGAGTCGAAACTCGCCAGTCTCCACTCCACTCCCAACCGTGGTGCCCCAC
  61 ---------+---------+---------+---------+---------+---------+ 120
     CCACCGACCCCCTCAGCTTTGAGCGGTCAGAGGTGAGGTGAGGGTTGGCACCACGGGGTG

GCGGGCCTGGGAGAGTCTGTGAGGCCGCCCACCGCTTGTCAGTAGAGTGCGCCCGCGAGC
 121 ---------+---------+---------+---------+---------+---------+ 180
     CGCCCGGACCCTCTCAGACACTCCGGCGGGTGGCGAACAGTCATCTCACGCGGGCGCTCG

CGTAAGCACAGCCCGGCAACATGCGGTCTTCAGACAGGAAAGTGGCCGCGAATGGGACCG
 181 ---------+---------+---------+---------+---------+---------+ 240
     GCATTCGTGTCGGGCCGTTGTACGCCAGAAGTCTGTCCTTTCACCGGCGCTTACCCTGGC
```

FIG. 1A

```
          GGGTGCCCAGCGGCTGTGGGGACTCTGTCCTGCGGAAACCGCGGTGACGAGCACAAGCTC
241       ----------+----------+---------+---------+---------+---------+ 300
          CCCACGGGTCGCCGACACCCCTGAGACAGGACGCCTTTGGCGCCACTGCTCGTGTTCGAG

GGTCAACTGGATGGGAATCGGCCTGGGGGGCTGGCACCGCGCCCACCAGGGGGTTTGCGG
301       ----------+----------+---------+---------+---------+---------+ 360
          CCAGTTGACCTACCCTTAGCCGGACCCCCCGACCGTGGCGCGGGTGGTCCCCCAAACGCC

CACTTCCCTCTGCCCCTCAGCACCCCACCCCTACTCTCCAGGAACGTGAGGTCTGAGCCG
361       ----------+----------+---------+---------+---------+---------+ 420
          GTGAAGGGAGACGGGGAGTCGTGGGGTGGGGATGAGAGGTCCTTGCACTCCAGACTCGGC

TGATGGTGGCAGGAAGGGGCCCTCTGTGCCATCCGAGTCCCCAGGGACCCGCAGCTGGCC
421       ----------+----------+---------+---------+---------+---------+ 480
          ACTACCACCGTCCTTCCCCGGGAGACACGGTAGGCTCAGGGGTCCCTGGGCGTCGACCGG

CCCAGCCATGTGCAAAGTATGTGCAGGGCGCTGGCAGGCAGGGAGCAGCAGGCATGGTGT
481       ----------+----------+---------+---------+---------+---------+ 540
          GGGTCGGTACACGTTTCATACACGTCCCGCGACCGTCCGTCCCTCGTCGTCCGTACCACA

CCCCTGAGGGGAGACAGTGGTCTGGGAGGGAGAGGTCCTGGACCCTGAGGGAGGTGATGG
541       ----------+----------+---------+---------+---------+---------+ 600
          GGGGACTCCCCTCTGTCACCAGACCCTCCCTCTCCAGGACCTGGGACTCCCTCCACTACC
```

FIG. 1B

```
      GGCAATGCTCAGCCCTGTCTCCGGATGCCAAAGGAGGGGTGCGGGGAGGCCGTCTTTGGA
601   ---------+---------+---------+---------+---------+---------+ 660
      CCGTTACGAGTCGGGACAGAGGCCTACGGTTTCCTCCCCACGCCCCTCCGGCAGAAACCT

GAATTCCAGGATGGGTGCTGGGTGAGAGAGACGTGTGCTGGAACTGTCCAGGGCGGAGGT
661   ---------+---------+---------+---------+---------+---------+ 720
      CTTAAGGTCCTACCCACGACCCACTCTCTCTGCACACGACCTTGACAGGTCCCGCCTCCA

GGGCCCTGCGGGGGCCCTCGGGAGGGCCCTGCTCTGATTGGCCGGCAGGGCAGGGGCGGG
721   ---------+---------+---------+---------+---------+---------+ 780
      CCCGGGACGCCCCCGGGAGCCCTCCCGGGACGAGACTAACCGGCCGTCCCGTCCCCGCCC

AATTCTGGCGGGCCACCCCAGTTAGAAAAAGCCCGGGCTAGGACCGAGGA
781   ---------+---------+---------+---------+---------+ 830
      TTAAGACCGCCCGGTGGGGTCAATCTTTTTCGGGCCCGATCCTGGCTCCT
               |         |                         |
              -35       -27                       -7
```

FIG. 1C

A schematic presentation of the plasmids containing the different promoters and enhancers.

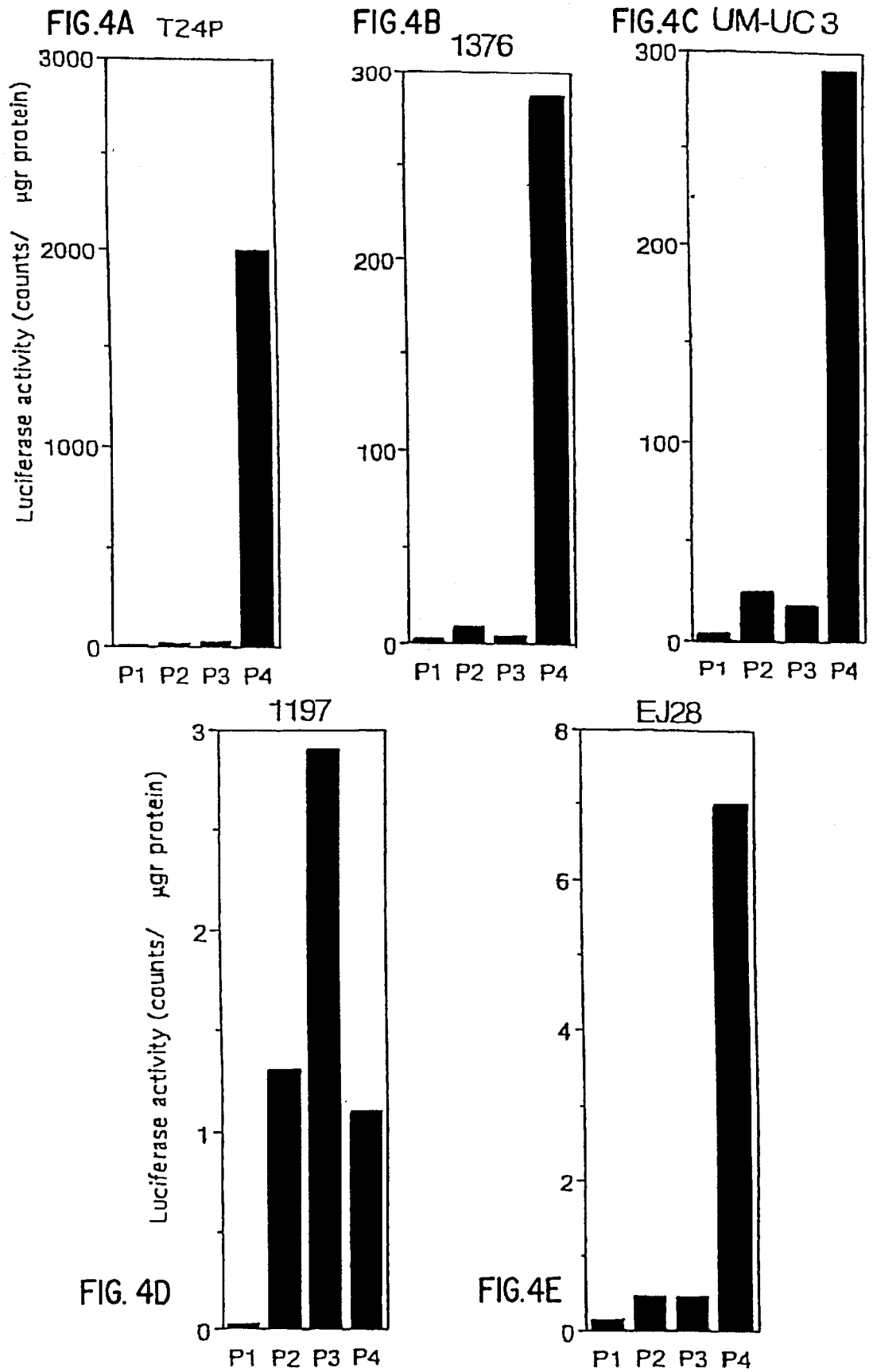

```
  1 GACAACCCTC ACCAAGGGCC AAGGTGGTGA CCGACGGACC CACAGCGGGG
 51 TGGCTGGGGG AGTCGAAACT CGCCAGTCTC CACTCCACTC CAACCGTGG
101 TGCCCCACGC GGGCCTGGGA GAGTCTGTGA GGCCGCCCAC CGCTTGTCAG
151 TAGAGTGCGC CCGCGAGCCG TAAGCACAGC CCGGCAACAT GCGGTCTTCA
201 GACAGGAAAG TGGCCGCGAA TGGGACCGGG GTGCCCAGCG GCTGTGGGA
251 CTCTGTCCTG CGGAAACCGC GGTGACGAGC ACAAGCTCGG TCAACTGGAT
301 GGGAATCGGC CTGGGGGGCT GGCACCGCGC CACCAGGGG GTTTGCGGCA
351 CTTCCCTCTG CCCCTCAGCA CCCCACCCCT ACTCCAGG AACGTGAGTT
401 CTGAGCCGTG ATGGTGGCAG GAAGGGGCCC TCTGTGCCAT CCGAGTCCCC
451 AGGGACCCGC AGCTGGCCCC CAGCCATGTG CAAAGTATGT GCAGGGCGCT
501 GGCAGGCAGG GAGCAGCAGG CATGGTGTCC CCTGAGGGGA GACAGTGGTC
551 TGGGAGGGAG AAGTCCTGGC CCTGAGGGAG GTGATGGGGC AATGCTCAGC
601 CCTGTCTCCG GATGCCAAAG GAGGGGTGCG GGGAGGCCGT CTTTGGAGAA
651 TTCCAGGATG GGTGCTGGGT GAGAGAGACG TGTGCTGGAA CTGTCCAGGG
701 CGGAGGTGGG CCCTGCGGGG GCCCTCGGGA GGGCCCTGCT CTGATTGGCC
751 GGCAGGGCAG GGGCGGGAAT TCTGGGCGGG GCCACCCCAG TTAGAAAAAG
801 CCCGGGCTAG GACCGAGGAG CAGGGTGAGG GAG
```

FIG. 5

1   CAAGGACATG GAATTTCGGA CCTTCTGTCC CCACCCTCTC TGCTGAGCCT

51  AGGAACCTCT GAGCAGCAGG AAGGCGTTGG GTCTAGAGCC TAGAAATGGA

101 CCCCCACGTC CACCTGCCCA GCCTAGACCC CCAGCATTGA AGGGTGGTCA

151 GACTTCCTGT GAGAGGAAGC CACTAAGCGG GATGGACACC ATCGCCCACT

201 CCACCCGGCC CTGCCCAGCC CTGCCCAGTC CAGCCCAGTC CAGCCCAGCC

251 CTGCCCTTCC CAGCCCTGCC CAGCCCAGCT CATCCCTGCC CTACCCAGCC

301 CAGCCCTGTC CTGCCCTGCC CAGCCCAGCC CAGCCCAGCC CTGCCCTGCC

351 CTGCCCTGCC CTTCCCAGCC CTGACCTTCC CAGCCCTGCC CAGCCCAGCT

401 CATCCCTGCC CTACCCAGCT CAGCCCTGCC CTGCCCTGCC CTGCCCTGCC

451 CAGCCCTACC CAGCCCAGCC CTGCCCTGCC CTGCCCAGCT CAGCCCTGCC

501 CACCCCAGCC CAGCCCAGCC CAGCATGCGT TCTCTGGATG GTGAGCACAG

551 GCTTGACCTT AGAAAGAGGC TGGCAACGAG GGCTGAGGCC ACCAGGCCAC

601 TGGGTGCTCA CGGGTCAGAC AAGCCCAGAG CCTGCTCCCC TGCCACGGGT

651 CGGGGCTGTC ACCGCCAGCA TGCTGTGGAT GTGCATGGCC TCAGGGCTGC

701 TGGCTCCAGG CTGCCCCCGC CCTGGCTCCC GAGGCCACCC CTCTTATGCC

751 ATGAACCCTG TGCCACACCC ACCTCTGAGC TGTCCCCGCT CCTGCCGCCT

801 GCACCCCCTG AGCAGCCCCC TGTGTGTTTC ATGGGAGTCT TAGCAAGGAA

851 GGGGAGCTCG AATTCCTGCA GCCCGGG

FIG. 6

1   CCGGGTACCG AGCTCCCAGG AAGATAAATG ATTTCCTCCT CTCTAGAGAT

51  GGGGGTGGGA TCTGAGCACT CAGAGCCAAG GGCGCAGTGG GTCCGGGCGG

101 GGGCCCTCCT CGGCCCTCCC AACATGGGGG CCAGGAGGTC AGCCCCTCAA

151 CCTGGACCCC GGCTGGGTCT CAGGGAATGG TCTCCCCCAG TGGCCCAGCT

201 TGCTTGTGTT TTCAGATGGG TGTGCATGGG TGTGTGTGTG TGTGTGTGTG

251 TGTGTGTGTG TGTGTGTGTG TGTGATGCCT GACAAGCCCC AGAGAGCCAA

301 AGACCTGAGT GGAgATCTTG TGACTTCTCA AAAGGGGGAT TGGAAGGTTC

351 GAGAAAGAGC TGTGGTCAGC CTTGCTCTCC CTTAAGGCTG TGGTAACCAC

401 ACTAGGCATA GCATAGGCCT GCGCCCCGTC CCTCCTTCCC TCCTCCGCGC

451 CTCTCCTTTC TCTTTCTCCC CCCTCTACCC CGCTCCCTGG CCTGCTCCTG

501 GTGACACCGT TGGCCCCCTT CCAGGGCTGA GGGAAGCCAG CGGGGGCCCC

551 TTCCTGAAAG CCCACCTGCA GGCCGGCTTG CTGGGAAGGG GCTGCTCTCG

601 CAgAGGCTCC CGCCCGCCCT GCAGCCGTTT CCTGgAAGCA GTCGCTGTGG

651 GTATTCTGTT CCTTGTCAGC ACTGTGCTTG CAAAgAAAGC AgACACTGTG

701 CTCCTTGTCC TTAGGGAGCC CCGCTCCATC ACCCAACACC TGGCTGGACA

751 CAGGCGGGAG GCCGGGTCCG CGGGGAgCGG CGCGGGGCTG GGGCCGGACC

801 ATTAAACACA CACGGGCGCC AGGCACTGCA GGCTCCTCCT CCTCCTCCTG

851 CCCAGCGCCT CTGCTCACAG GCACGTGCCA AgCCCCTAGG CCAggAgGCC

901 AgCAgTGGGT GCAgAACAAG CTCCTGGGAA GGGGGTGCAg GGcGGACCCC

951 CGGGGAgAAG GGCTGGCAGG GCTGTGGGGG ACGCTGACCG TGGGCCCCAC

FIG. 7A

```
1001  GTTGCAgAAA ACTGGNTGCC TGgCTGGAAG ATGGGGGAGA TGCCAAGCCT
1051  CTGAGGCAGC ACGAgCAGGG TGCATGGAGG CCGGGGCGCG GGGAGGCTGC
1101  ACTGCAGCAT GCACCCCAAA GCCCANAGGG AGTGGAgACC AGGCCCTGGA
1151  ATCgAGAAGT AgAAAGGCGG CTTGGAGGCC TCGGAACCGG CTGACCTCCA
1201  ACAGAgTGGG TCTCCAGCCT GgcTCTGCCC TGCCGCAGGT CCCCTCCCcT
1251  CATTACCAGG CCTAGAGCCT CCAGTCCCGG TGGCCCCCAG CCcGAGGGTG
1301  AACGGCCTCA CCCTGGGTcG TGGGACAGAG GCACGTTCA TCAAGAGTGG
1351  CTCCCAAGGG ACAcGTGGCT GTTTGCAGTT CACAGGAAGC ATTcGAGATA
1401  AGGAGcTTGT TTTCCCAGTG GGCAcGGAGC CAGCAGGGGG GCTGTGGGGC
1451  AGCCCAGGGT GCAAGGcCAG GcTGTGGGGC TGCAGcTGCc TTGGGCCCCA
1501  CTCCCAGGCC TTTGCGGGAG GTGGGAGGCG gGAGGCGGCA GCTGCACAGT
1551  GGCCCCAGGC GAGGCTCTCA GCCCCAGTCG CTCTCCGGGT GGGCAGCCCA
1601  AGAGGGTCTG GCTGAGCCTC CCACATCTGG GACTCCATCA CCCAACAACT
1651  TAATTAAGGC TGAATTTCAC GTGTCCTGTG ACTTGGGTAG ACAAAGCCCC
1701  TGTCCAAAGG GGCAGCCAGC CTAAGGCAGT GGGGACGGCG TGGGTGGCGG
1751  GCGACGGGGG AGATGGACAA CAGGACCGAG GGTGTGCGGG CGATGGGGGA
1801  GATGGACAAC AGGACCGAGG GTGTGCGGGC GATGGGGGAG ATGGACAACA
1851  GGACCGAGGG TGTGCGGGAC ACGCATGTCA CTCATGCACG CCAATGGGGG
1901  GCGTGGGAGG CTGGGGAGCA GACAGACTGG GCTGGGCTGG GCGGGAAGGA
1951  CGGGCAGATG
```

FIG. 7B

```
   1 CCGGGTACCG AGCTCCCAGG AAGATAAATG ATTTCCTCCT CTCTAGAGAT
  51 GGGGGTGGGA TCTGAGCACT CAGAGCCAAG GGCGCAGTGG GTCCGGGCGG
 101 GGGCCCTCCT CGGCCCTCCC AACATGGGGG CCAGGAGGTC AGCCCCTCAA
 151 CCTGGACCCC GGCTGGGTCT CAGGGAATGG TCTCCCCCAG TGGCCCAGCT
 201 TGCTTGTGTT TTCAGATGGG TGTGCATGGG TGTGTGTGTG TGTGTGTGTG
 251 TGTGTGTGTG TGTGTGTGTG TGTGATGCCT GACAAGCCCC AGAGAGCCAA
 301 AGACCTGAGT GGAgATCTTG TGACTTCTCA AAAGGGGGAT TGGAAGGTTC
 351 GAGAAAGAGC TGTGGTCAGC CTTGCTCTCC CTTAAGGCTG TGGTAACCAC
 401 ACTAGGCATA GCATAGGCCT GCGCCCCGTC CCTCCTTCCC TCCTCCGCGC
 451 CTCTCCTTTC TCTTTCTCCC CCCTCTACCC CGCTCCCTGG CCTGCTCCTG
 501 GTGACACCGT TGGCCCCCTT CCAGGGCTGA GGGAAGCCAG CGGGGGCCCC
 551 TTCCTGAAAG CCCACCTGCA GGCCGGCTTG CTGGGAAGGG GCTGCTCTCG
 601 CAgAGGCTCC CGCCCGCCCT GCAGCCGTTT CCTGgAAGCA GTCGCTGTGG
 651 GTATTCTGTT CCTTGTCAGC ACTGTGCTTG CAAAgAAAGC AgACACTGTG
 701 CTCCTTGTCC TTAGGGAGCC CCGCTCCATC ACCCAACACC TGGCTGGACA
 751 CAGGCGGGAG GCCGGGTCCG CGGGGAgCGG CGCGGGGCTG GGGCCGGACC
 801 ATTAAACACA CACGGGCGCC AGGCACTGCA GGCTCCTCCT CCTCCTCCTG
 851 CCCAGCGCCT CTGCTCACAG GCACGTGCCA AgCCCCTAGG CCAggAgGCC
 901 AgCAgTGGGT GCAgAACAAG CTCCTGGGAA GGGGGTGCAg GGcGGACCCC
 951 CGGGGAgAAG GGCTGGCAGG GCTGTGGGGG ACGCTGACCG TGGGCCCCAC
1001 GTTGCAgAAA ACTGGNTGCC TGgCTGGAAG ATGGGGGAGA TGCCAAGCCT
1051 CTGAGGCAGC ACGAgCAGGG TGCATGGAGG CCGGGGCGCG GGGAGGCTGC
1101 ACTGCAGCAT GCACCCCAAA GCCCANAGGG AGTGGAgACC AGGCCCTGGA
1151 ATCgAGAAGT AgAAAGGCGG CTTGGAGGCC TCGGAACCGG CTGACCTCCA
1201 ACAGAgTGGG GCCGGCCCTG GAGGCAAAGA GGTGCCCGGG GTCCGGCCCT
1251 GCCTGGGGGA GCTATGTGTC ATGGGCAAGC CACAGGATAT GTagCCCGCT
1301 CTGagCCTAT GGACCCagGG CAGGGCTGCA AGGCAGGGCA GGGGAGACAG
1351 CACGGGGGAG CAAGGAGCAG AGAGGGGGCC TCAGGCTCTC CCAGGAGGAA
1401 CATTCTCCCG ACAGGAGGAA GAGACGGCCC AGGGGTGACT GTGGGGAGCC
1451 ATGGTGGCAG CTGGGGTCGT GGCAGATGGG AGAGAGGCTG GCGAGGTGAA
1501 GGTGCAGGGG TCAGGGCTCT GGGGCCCACA TGCCTGTGGG AGCAGGCAGG
```

FIG. 8A

1551 CCCAGGGCTC TCCGCCACTC CCCACTCCCG CTTGGCTCAT AGGCTGGGCC
1601 CAAGGGTGGG GTGGGATGAG CAGGAGATGG GGCCCAGGGG GCAAGCAGGG
1651 CCCCAAAGAC ATTTAGAAAA ACCGGTTTAT GCAGGCAGCA TTCAGAGCAG
1701 GCGGCGTGCG TGGCGGGGGC CCTGGGAGCA CAGAGAGGCA CACGTAGGGC
1751 CCCCGAGGGG CTCCCCATTG GCCGGCAGTG ACATCACCCC TGTGTCAACA
1801 GTGATGTCTG CAGCTCCGGC CAGCCAGGGT TTATGGAGCG AGACCCAGCC
1851 CGGCCTGGGC CCTCACTCCC CAGGCCCACA CACTAGCCCA CTGTTCAGGG
1901 TCCGGGGTGG CGGCATGGCC TGGGGTCCT GGCACCGCTG CTCCTCTGCC
1951 CACCCTAACT TCCCGGCATG GCGGCTGCCC CCTCTGAGCG TCCCCAACCA
2001 GTAAGTGTGG GGCCCAGCAG gCCTGCcGTC CTCcTCcTCT TCCCCTcTAG
2051 AGAGAAACGT GGAGGTCCTG GGGCTGGGGG CGCTCATAGC CcTGTGACAC
2101 AGGTGCATGG GGTCAGGGGT CCCAGAATGG CCCCTGGGAA GGACCTCAGC
2151 TGGGCCGGCG GCTcTAGGCT TCAGGGGTCT GTCTGCACAG GGGNTAGCCC
2201 CTCCCAGACC TCTGTGAAGC CAGTACGGGC CTCCCCTCCC TGCCCCGTGC
2251 TCTGTCCGGT GCTTCCTGGA CTGCACTGCG GGCCACTGGT GAGAGGGTGG
2301 ACAGGGAAGG GCCGCCGTGG TGCCTGTTCC TGCCCACCTG GCTGTGTGGT
2351 CCCCTCCAAG TAGGGACAAC CCTTCTGAGG GCTTGGGGGC ACCCTGGGGT
2401 TGCCAGGGCC TCCCAGAGCC CTGTGAGCCC CTGGGGGGTC TGGCCTGATG
2451 CCCCCCTCCA CGTCCAGGGC CGGCTGTGGC CCAGAACCCC AGCTTCCCAG
2501 CAGGCCGGTG TGCGGTGGTG ACCCAGGAGA GGCCTCGCCT CCACTGAGGG
2551 GCCACCGACC TCTGTCAGAC CACAGAGACC CCCAAGGAgT cTGAAGGCTG
2601 GAGACCCGGG GCTGGGACCA GGTGGGAcTT TCCCACGGAG CCGTCCCCAG
2651 GCCCAGCTGG GGACAcGTCC CCcTTcTcTC CAGACACACC CTGCcTGCCA
2701 CCAGGACACA CCGGCCTGTT GGGGGTcTcT TTTAAGTGCT TGCCACTCTG
2751 AGGTGAcTGT CCCTTTCCAA AGAGGTTTcT GGGGCCCAGG TGGGAtGCGT
2801 CGGCCTGAGC AGGAGGATcT GGGCCGCCAG GGGCTGGGGA CTGTcTCCTG
2851 GGGAAGGAAG CGCCTGGGAG CGTGTGTGCT GACCCAGGAC CATCCAGGGA
2901 GGCCCGTcTG TGGGGCAAGC GGGAAGGGAG CGGCTGGAGA GGCTTGGCCG
2951 CCCCCGCCCT GCCTCCCATT CCTTAGcTCC ATGCCTGTCA ACCTcTGTCA

FIG.8B

3001 CCCAGTGAGT GATGTCCAGG GGCCCTGGAA AGGTCACAGC ATGTTTGAGC

3051 GGGGTGAGAG AGAGGGGAAA GGCGGGGGCG GGGAAAAGTA cGTGGAGGAA

3101 GCTTTAGGCC CAAGGAAGGA GACAGGGTTc TGGGAGGGAG GGAGCCACTG

3151 GGGCCGCCGG GAAGGTCCCT GCTTGCTGCT GCCACCCAGA ACCCTCGCCT 3201 cTTAGcTAGC CCCcGCAGCC CCAGCcTTTc TGGCNTGTGg CCCTCTCCCC

3251 CATCCCCAGG TGTCcTgTGC AACCAGGCcT TGGACCCAAA CCCTCcTGCC

3301 CCCTCcTCTC CCTCCTCACC CTCCCAATGC AGTGGTCTCC AGCCTGgcTC

3351 TGCCCTGCCG CAGGTCCCCT CCCcTCATTA CCAGGCCTAG AGCCTCCAGT

3401 CCCGGTGGCC CCCAGCCcGA GGGTGAACGG CCTCACCCTG GGTcGTGGGA

3451 CAGAGGGCAC GTTCATCAAG AGTGGCTCCC AAGGGACAcG TGGCTGTTTG

3501 CAGTTCACAG GAAGCATTcG AGATAAGGAG cTTGTTTTCC CAGTGGGCAc

3551 GGAGCCAGCA GGGGGGCTGT GGGGCAGCCC AGGGTGCAAG GcCAGGcTGT

3601 GGGGCTGCAG cTGCcTTGGG CCCCACTCCC AGGCCTTTGC GGGAGGTGGG

3651 AGGCGgGAGG CGGCAGCTGC ACAGTGGCCC CAGGCGAGGC TCTCAGCCCC

3701 AGTCGCTCTC CGGGTGGGCA GCCCAAGAGG GTCTGGCTGA GCCTCCCACA

3751 TCTGGGACTC CATCACCCAA CAACTTAATT AAGGCTGAAT TTCACGTGTC

3801 CTGTGACTTG GGTAGACAAA GCCCCTGTCC AAAGGGGCAG CCAGCCTAAG

3851 GCAGTGGGGA CGGCGTGGGT GGCGGGCGAC GGGGGAGATG GACAACAGGA

3901 CCGAGGGTGT GCGGGCGATG GGGGAGATGG ACAACAGGAC CGAGGGTGTG

3951 CGGGCGATGG GGGAGATGGA CAACAGGACC GAGGGTGTGC GGGACACGCA

4001 TGTCACTCAT GCACGCCAAT GGGGGGCGTG GGAGGCTGGG GAGCAGACAG

4051 ACTGGGCTGG GCTGGGCGGG AAGGACGGGC AGATG

FIG. 8C

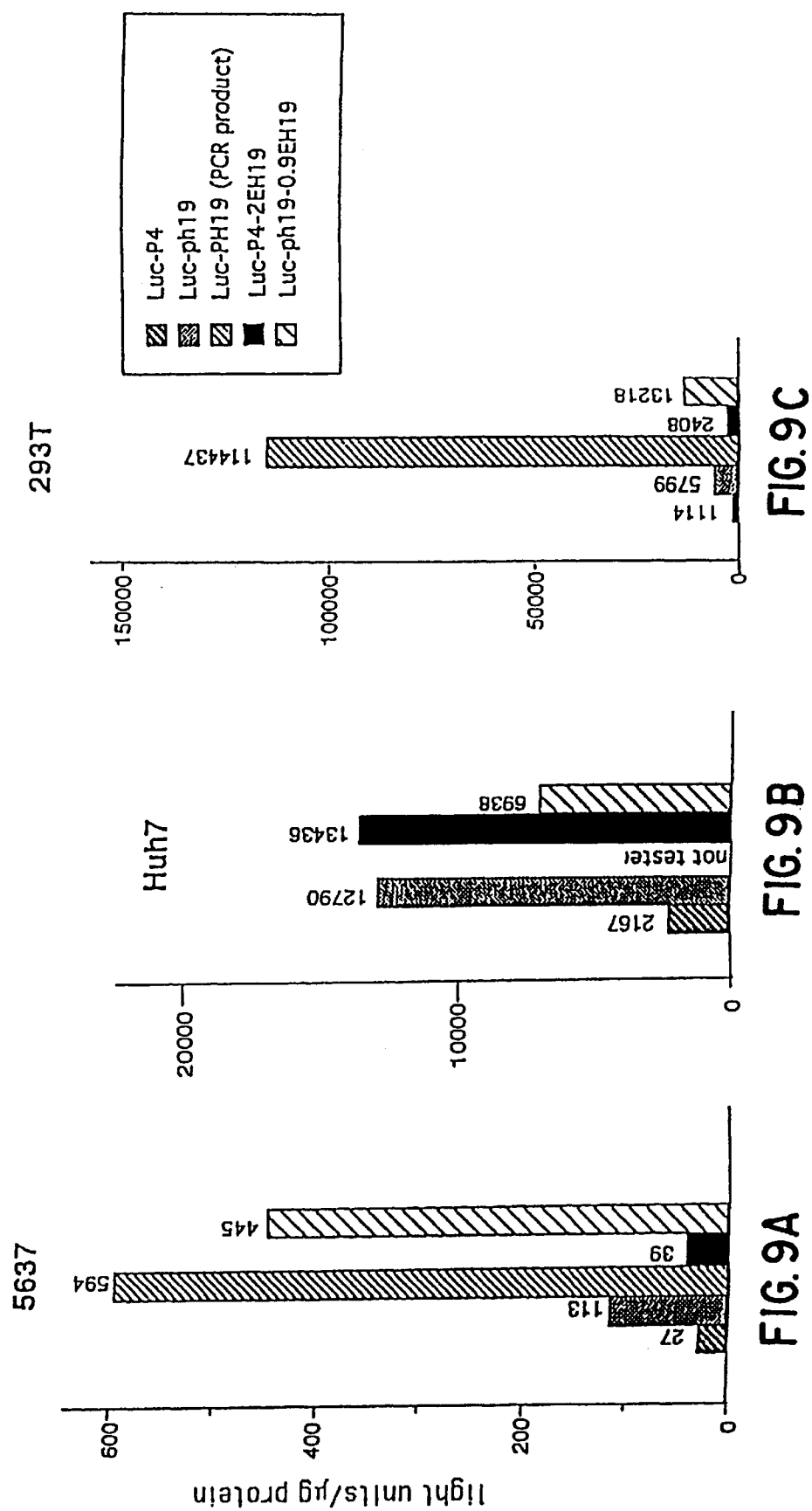

METHODS AND COMPOSITIONS FOR INDUCING TUMOR-SPECIFIC CYTOTOXICITY

The present application is a divisional of application Ser. No. 09/165,240 filed Oct. 1, 1998, now U.S. Pat. No. 6,087,164 which is a CIP of Ser. No. 08/943,608, filed Oct. 3, 1997, now abandoned, which is incorporated by reference herein in its entirety.

1. FIELD OF THE INVENTION

The invention is in the field of tumor cell biology and cancer treatment. More specifically, the invention relates to the specific expression of heterologous genes, particularly genes encoding cytotoxic products, in tumor cells.

2. BACKGROUND OF THE INVENTION

2.1 The H19 Gene

The H19 gene is one of the few genes known to be imprinted in humans (Hurst et al., 1996, Nature Genetics 12:234–23). At the very beginning of embryogenesis, H19 is expressed from both chromosomal alleles (DeGroot et al., 1994, Trophoblast 8:285–302). Shortly afterwards, silencing of the paternal allele occurs, and only the maternally inherited allele is transcribed.

H19 is abundantly expressed during embryogenesis, and was first identified as a gene that was coordinately regulated with alpha-fetoprotein in liver by the trans-acting locus raf (Pachnis et al., 1984, Proc. Natl. Acad. Sci. USA 81:5523–5527). Additionally, H19 has been independently cloned by a number of groups using screens aimed at isolating genes expressed during tissue differentiation. For example, Davis et al. (1987, Cell 51:987–1000) identified the mouse homolog of H19 in a screen for genes active early during differentiation of C3H10T1/2 cells. Pourier et al. (1991, Development 113:1105–1114) found that murine H19 was expressed during stem cell differentiation and at the time of implantation. Transcription of the human H19 gene was also discovered in differentiating cytotrophoblasts from human placenta (Rachmilewitz et al., 1992, Molec. Reprod. Dev. 32:196–202).

While transcription of H19 RNA occurs in a number of different embryonic tissues throughout fetal life and placental development, H19 expression is down-regulated postnatally. Relatively low levels of H19 transcription have been reported, however, in murine adult muscle and liver (Brunkow and Tilghman, 1991, Genes & Dev. 5:1092–1101). H19 also is activated postnatally in cancer cells. Ariel et al. (1997, Molec. Pathol. 50:34–44) demonstrated H19 expression in a number of tumors arising from the tissues in which it is expressed prenatally. Additionally, these authors found H19 RNA in tumors derived from neural tissues, in particular astrocytoma and ganglioneuroblastoma, that are not known to be associated with H19 expression. Given the large array of cancers expressing H19 RNA, these authors speculated that H19 was an oncofetal RNA and proposed investigating H19 as a tumor marker for human neoplasia.

Both human and murine H19 genes have been cloned and sequenced (Brannan et al., 1990, Molec. Cell. Biol. 10:283–6). Comparison of the human and mouse H19 genes revealed an overall 77% nucleotide sequence identity. Despite this conservation of nucleotide homology between species, very low deduced amino acid sequence identity could be predicted from the open reading frames of the two genes (Id.). Further, although H19 RNA is transcribed by RNA polymerase II, spliced and polyadenylated, it does not appear to be translated. Instead, H19 RNA has been found associated with the 28S cytoplasmic RNA, leading to speculation that H19 RNA may function as an RNA component of a ribonucleoprotein (Id.).

The actual physiological role of H19 is not fully understood. H19 can act as a dominant lethal gene; a high ectopic expression of an H19 transgene causes lethality in mice shortly before birth (Brunkow et al., supra). This lethal period coincides with the time when H19 transcription becomes repressed. On the other hand, no defect has been observed in either heterozygous or homozygous mice carrying an H19 knockout allele(s) (Leighton et al., 1995, Nature 375:34–39). A knockout of the maternally inherited allele does interfere with imprinting of the genetically linked and oppositely imprinted IGF-2 gene; the resulting mice are larger at birth than their littermates due to the increased prenatal expression of IGF-2 (Id.). Since these two oppositely imprinted genes share cis-acting regulatory sequences, Leighton and colleagues speculated that H19 may be involved in imprinting the IGF-2 gene.

Another function proposed for the H19 gene product is that of a tumor suppressor RNA. Hao et al. (1993, Nature 365:764–767) reported that transfection of two embryonal tumor cell lines, RD and G401, with an H19 expression construct resulted in cell growth retardation, morphological changes and reduced tumorigenicity in nude mice. Such a tumor suppressor activity has been noted as consistent with the observed lethality of ectopic expression in mice (Hao et al., supra) as well as the increased size of mice that are knocked out for the maternal H19 allele (Leighton et al., supra). The proposal that H19 is a tumor suppressor has been controversial, however. Some of the results were reportedly not reproduced, and there may exist another candidate tumor suppressor gene closely linked to H19 (Ariel et al., supra). H19's proposed role as a tumor suppressor also conflicts with the experimental data that H19 is activated in a broad array of tumor cells (see for example Lustig-Yariv et al., 1997, Oncogene 23:169–177).

2.2 The Insulin-Like Growth Factor (IGF) Genes

IGF-2 is another imprinted gene whose expression depends upon it's parental origin. However in contrast to H19, IGF-2 in both mice and humans is maternally imprinted and therefore expressed from the paternally inherited allele (Rainier et al., 1993, Nature 363:747–749). The human IGF-2 gene exhibits a complex transcriptional pattern. There are four IGF-2 promoters that are activated in a tissue and developmentally specific manner. Only three of the promoters, P2, P3 and P4 are imprinted and active during fetal development and in cancer tissues. The fourth, promoter P1, is not imprinted and is activated only in adult liver and choroid plexus (see Holthuizen et al., 1993, Mol. Reprod. Dev. 35:391–393). The P3 promoter of the IGF-2 gene has been implicated in the progression of liver cirrhosis and hepatocellular carcinoma (Kim and Park, 1998, J. Korean Med. Sci. 13:171–178).

Loss of imprinting of IGF-2 has been implicated in Wilm's tumor (Ogawa et al., 1993, Nature 363:749–751). This observation led many investigators to speculate that the loss of imprinting and biallelic expression of imprinted genes may be involved in growth disorders and the development of cancer (see also Rainier et al., 1993, Nature 362:747–749, and Glassman et al., 1996, Cancer Genet. Cytogenet. 89:69–73).

2.3 Tumor-Specific Gene Therapy

Regulatory sequences from tumor-associated genes have been used to selectively target expression of a suicide gene in tumor-derived cells. For example, alpha-fetoprotein expression is induced in hepatocellular carcinoma. Huber et al. (1991, Proc. Natl. Acad. Sc. USA 88:8039–8043) used control sequences from either the albumin gene or the alpha-fetoprotein gene to target expression of varicella-zoster thymidine kinase (VZV TK) gene coding sequences to hepatoma cells. Hepatoma cells infected in vitro with a retroviral vector containing one of these expression constructs expressed VZV TK and became sensitive to the normally non-toxic prodrug 6-methoxypurine arabino-nucleoside (araM). Kaneko et al. (1995, Cancer Res. 55:5283–5287) constructed an adenoviral vector expressing HSV TK under the control of the alpha-fetoprotein control sequences. Recombinant adenoviral particles containing this vector were directly injected into hepatocellular carcinoma-derived tumors generated in athymic nude mice. Subsequent intraperitoneal injections with ganciclovir caused regression of the hepatocellular carcinoma-derived tumors.

Osaki et al. (1994, Cancer Res. 54:5258–5261) transfected into A549 lung carcinoma cells an expression construct containing the control sequences for the lung carcinoembryonic antigen gene linked to the coding sequence for Herpes simplex virus thymidine kinase (HSV TK). The transfected cells were sensitive to ganciclovir. Additionally, tumor growth in nude mice from subcutaneously injected transfected cells was inhibited by repeated intraperitoneal injections of ganciclovir. However, the carcinoembryonic antigen gene has recently been described as expressed in normal colonic mucosa, thus limiting the usefulness of these control sequences as tumor specific regulatory regions (Osaka et al., supra). Thus, there remains a need for the development of gene therapy vectors that specifically express gene products in tumor cells.

3. SUMMARY OF THE INVENTION

The invention relates to methods and compositions for inducing selective expression of heterologous genes in tumor cells. In particular, the invention relates to polynucleotides comprising a regulatory transcriptional sequence operatively linked to heterologous genes which result in tumor-specific expression of the heterologous genes. More particularly, the regulatory transcriptional sequence is derived from a genomically imprinted gene that is specifically expressed in cancer cells such as the H19, and the IGF-2 P3 and P4 promoters, and the heterologous gene encodes a cytotoxic protein or cytostatic gene product. In another embodiment of the invention, the IGF-1 promoter is operatively linked to a heterologous gene to result in tumor-specific expression of the gene. The regulatory sequences will direct gene expression in a number of different cancerous cell types. Such methods and compositions are useful in the treatment of a wide variety of cancers and hyperproliferative conditions.

One aspect of the invention are expression vectors containing polynucleotides comprising such regulatory regions operatively linked to heterologous genes. Particularly preferred regulatory regions are those encoding H19 regulatory regions such as promoter and enhancer sequences, the IGF-2 P3 or P4 promoter or an IGF-1 promoter. In that connection, the H19 enhancer and active portions thereof may be used in any combination with H19 promoter, IGF-1 promoter, IGF-2 P3 promoter or IGF-2 P4 promoter. Also encompassed by the invention are host cells containing such vectors. In that regard, an expression construct containing a heterologous gene controlled by H19 promoter with or without H19 enhancer may be co-introduced into a cell with a second construct containing a heterologous gene controlled by IGF-1 promoter or IGF-2 P3 or P4 promoter in combination with the H19 enhancer. In another aspect, the invention provides methods of using such vectors to express heterologous genes in tumor cells. Yet another aspect of the invention is the treatment of cancer using the vectors of the invention in gene therapy.

4. BRIEF DESCRIPTION OF THE FIGURES

FIGS. 1A–1C. The nucleotide sequence of human H19 promoter region. The promoter region from nucleotide position –837 to –7 (relative to the start of transcription) is shown (SEQ ID NO:1).

FIG. 2. Schematic diagram of the vectors used to express a heterologous gene under the control of H19 regulatory sequences.

Figure 3A:
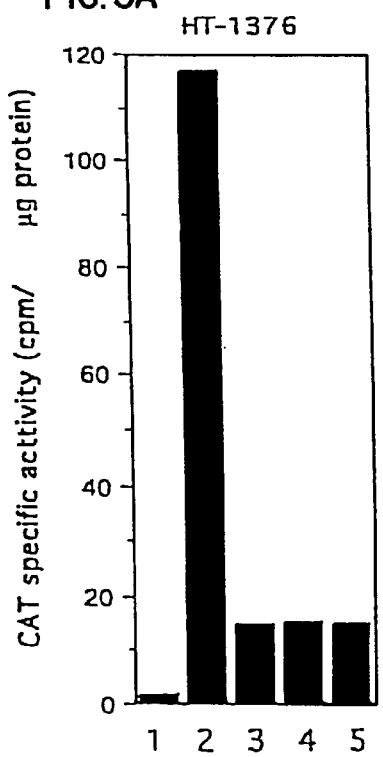
Figure 3B:
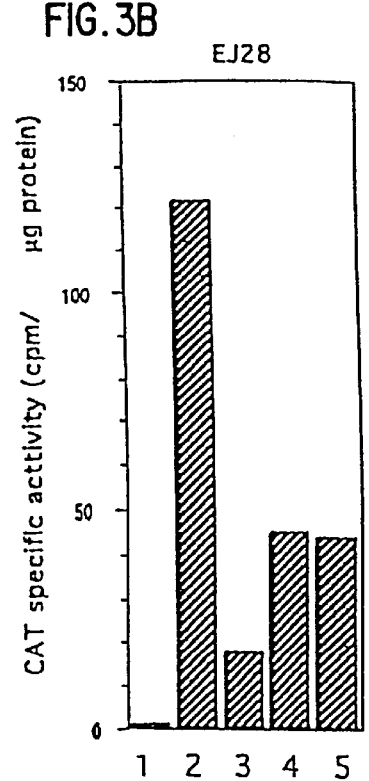
Figure 3C:
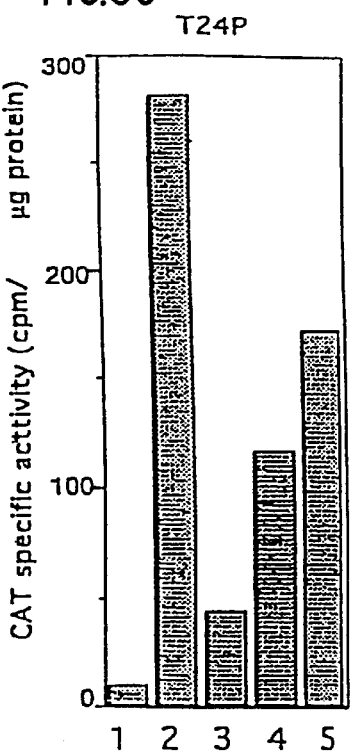
Figure 3D:
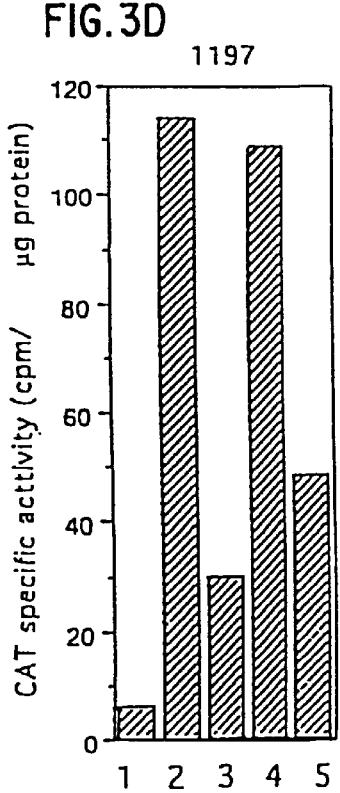
Figure 3E:
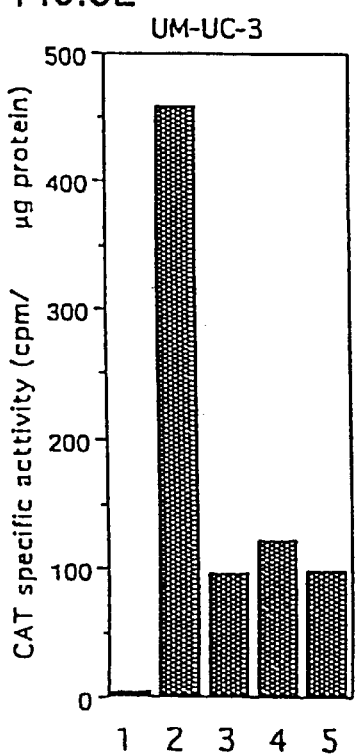

FIGS. 3A–3E. H19 Regulatory Sequences Direct Expression Of A Heterologous Gene (CAT) in Bladder Cancer Cell Lines. For the five different indicated cell lines, CAT specific activity (cpm/μg protein) is plotted as a function of the vector used for transfection. FIG. 3A: HT-1376 cells. FIG. 3B: EJ28 cells. FIG. 3C: T24P cells. FIG. 3D: 1197 cells. FIG. 3E: UM-UC-3 cells. The vectors, as follows, are described more fully below in Section 6: (1) pCAT-basic; (2) pCAT-control; (3) pH19E; (4) pH19EH19D; and (5) pH19EH19R.

FIGS. 4A–4E. The IGF-2 P3 and P4 Promoters Direct Expression Of A Heterologous Gene (Luciferase) In Bladder Cancer Cell Lines. For the five different cell lines shown, luciferase specific activity (counts per μg of protein) is plotted as a function of the IGF-2 promoter used in the transfected construct to direct expression of luciferase. FIG. 4A: T24P cells. FIG. 4B: 1376 cells. FIG. 4C: UM-UC3 cells. FIG. 4D: 1197 cells. FIG. 4E: EJ28 cells. The vectors are described more fully below in Section 10.

FIG. 5: Nucleotide sequence of a Human H19 promoter fragment (SEQ ID NO:2).

FIG. 6: Nucleotide sequence of the 0.9 kb H19 enhancer fragment (SEQ ID NO:3).

FIGS. 7A and 7B: Nucleotide sequence of the 2 kb H19 enhancer fragment (SEQ ID NO:4).

FIGS. 8A–8C: Nucleotide sequence of the 4 kb H19 enhancer fragment (SEQ ID NO:5).

FIGS. 9A–9C: Transfection with vectors containing various H19 regulatory region and P4 promoter combinations directs luciferase expression in tumor cells. FIG. 9A: 5637 cells. FIG. 9B: Huh7 cells. FIG. 9C: 293T cells.

Figure 10A:
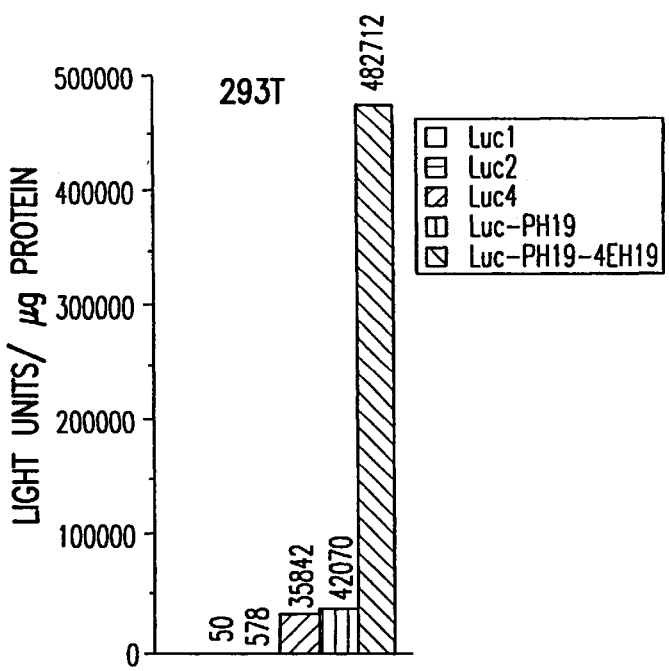
Figure 10B:
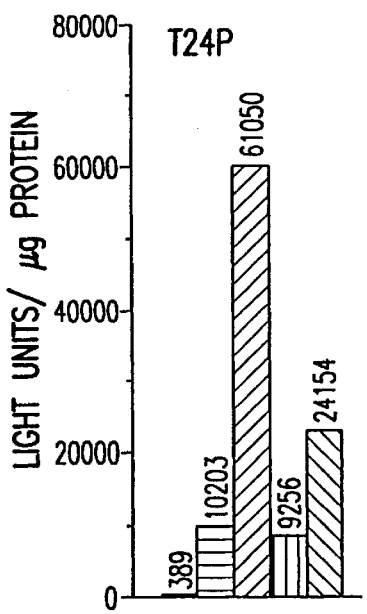
Figure 10C:
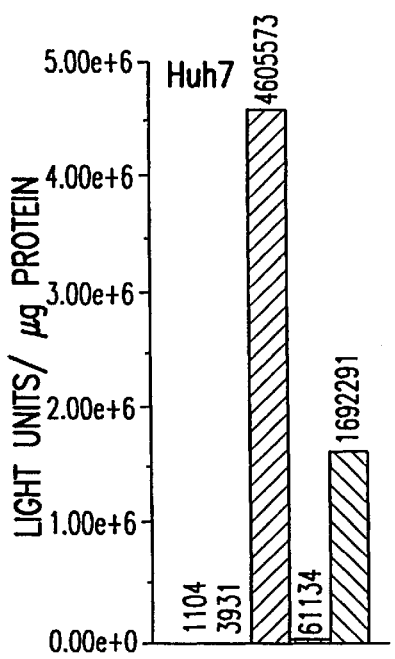
Figure 10D:
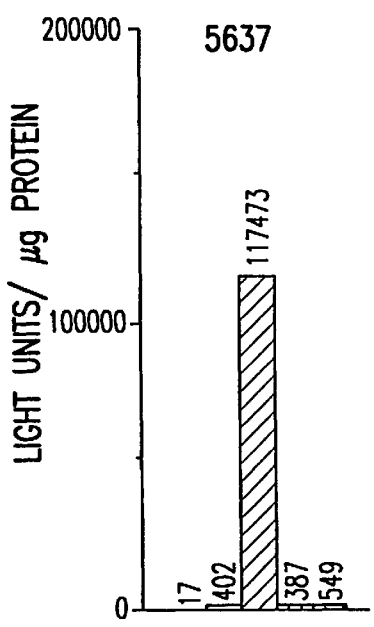
Figure 10E:
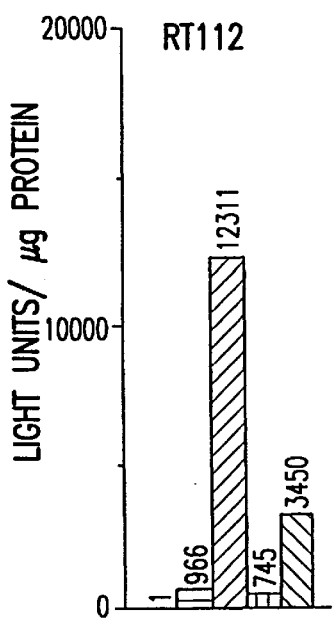

FIGS. 10A–10E: Transfection with vectors containing H19 regulatory regions direct luciferase expression in tumor cells. FIG. 10A: 293T cells. FIG. 10B: T24P cells. FIG. 10C: Huh7 cells. FIG. 10D: 5637 cells. FIG. 10E: RT112 cells.

5. DETAILED DESCRIPTION OF THE INVENTION

The invention is based, in part, on the discovery that the regulatory regions from genomically imprinted genes that are expressed in cancer cells can be used to target the expression of coding sequences of interest in cancer cells. In particular, it has been found that H19 expression is activated in a wide array of carcinomas, including but not limited to bladder carcinoma, hepatocellular carcinoma, hepatoblastoma, rhabdomyosarcoma, ovarian carcinoma, cervical carcinoma, lung carcinoma, breast carcinoma, squamous cell carcinoma in head and neck, esophageal carcinoma, thyroid carcinoma, astrocytoma, ganglioblastoma and neuroblastoma. Further, it has been discovered that constructs containing the H19 promoter regions operatively linked to a heterologous gene, or the IGF-2 P3 or P4 promoter operatively linked to a heterologous gene, or constructs containing such a promoter in combination with a downstream H19 enhancer, are specifically activated in tumor cells. In another aspect of the invention, an IGF-1 promoter is used to direct expression of the heterologous gene.

Accordingly, in one of its aspects, the invention provides methods and compositions for altering the phenotype of, or selectively killing, cancerous cells. This object is accomplished by delivering to the cells a polynucleotide comprising the regulatory regions from genomically imprinted genes that are expressed in cancer cells operably linked to a heterologous gene. The heterologous gene can encode, for example, a cytostatic or a cytotoxic agent (e.g. a toxin, an antisense RNA or a ribozyme).

Regulatory regions from genomically imprinted genes that are expressed in cancer cells include but are not limited to the H19 promoter and enhancer, and the IGF-2 P3 and P4 promoter.

For purposes of the invention described herein, the term "operatively linked" means that a nucleotide sequence is linked to a regulatory sequence in a manner which allows expression of the nucleotide sequence to be directed by the regulatory sequence.

A "heterologous" gene sequence refers, for purposes of the instant application, to a gene sequence that is not normally operatively linked to the regulatory sequences of the H19 gene. Generally, heterologous gene sequences include sequences that encode cytostatic and cytotoxic gene products.

As used herein, the term "expression" refers to the transcription of the DNA of interest, and the splicing, processing, stability, and, optionally, translation of the corresponding mRNA transcript. Depending on the structure of the DNA molecule delivered, expression may be transient or continuous.

5.1 Regulatory Seguences of the H19 gene, the IGF-2 P3 and P4 Promoters and IGF-1 Promoter Described herein are H19 regulatory sequences that can be used to direct the tumor cell specific expression of a heterologous coding sequence. These H19 regulatory sequences include the upstream H19 promoter region and/or the downstream H19 enhancer region. The nucleotide sequence of one H19 promoter region is shown in FIGS. 1A–1C (SEQ ID NO: 1). This 830 nucleotide sequence extends from −837 to −7 nucleotides from the cap site (as described in Brannan et al., supra). A consensus TATA sequence occurs at nucleotides −27 to −35. Two consensus AP2 binding sites (8/9 matches) occur at approximately −500 and −40 nucleotides upstream from the initiation of transcription. When placed upstream of the coding region for a heterologous gene, as discussed in more detail below, approximately 830 base pairs of the regulatory region is sufficient to direct expression of the operatively linked heterologous gene in cancer cells that also express endogenous H19. Additionally, another H19 promoter region between nucleotides −819 to +14 (FIG. 5, SEQ ID NO:2) is also sufficient to direct expression of the operatively linked heterologous gene in cancer cells.

The downstream enhancer region of the human H19 gene can optionally be added to an H19 promoter/heterologous gene construct in order to provide enhanced levels of tumor cell-specific expression. As described more fully below and illustrated by way of example in Section 6, the downstream enhancer region is encompassed on a SacI restriction fragment extending from +6 kb to +11 kb relative to the start site of transcription. As expected from an enhancer sequence, the downstream enhancer is able to exert its effect when placed in either reverse or direct orientation (relative to the orientation of the H19 enhancer in the endogenous H19 gene) downstream from the coding region of a heterologous gene under the control of the H19 promoter. Additionally, fragments of this enhancer containing the sequences as shown in FIGS. 6, 7A, 7B and 8A–8C (SEQ ID NOS:3–5) may also be used to facilitate gene expression.

The expression of the IGF-1 gene has been associated with lung cancer and breast cancer. The IGF-1 promoter (nucleotide sequence between nucleotides 1 to 1630 in the human IGF-1 gene sequence (Genbank accession number M12659 M77496 incorporated herein by reference; Rotwein et al., 1986, J. Biol. Chem. 261:4828–4832).

The IGF-2 gene product is expressed using one of four different promoter regions. Three of these four promoters are imprinted and are expressed in embryonic tissues; promoter P1, however, is activated in adult tissues only (Sussenbach et al., 1992, Growth Reg. 2:1–9). The P3 promoter has been implicated in hepatocarcinoma. It has also been discovered that the imprinted P4 promoter (nucleotide sequence −546 to +102 of the IGF-2 gene) and P3 promoter (nucleotide sequence −1229 to +140 of IGF-2 gene) are activated in human bladder cancer cells, and may be used to direct expression of an operatively linked heterologous gene to tumor cells. The IGF-2 P3 and P4 promoters may be used in combination with the H19 enhancer or active fragments thereof.

These regulatory sequences from genomically imprinted and non-imprinted genes that are expressed in cancer cells can be further delineated to define the minimal regulatory sequences required to obtain the desired tumor specific expression. For example, the promoter region may be altered by additions, substitutions or deletions and assayed for retention of tumor specific expression function. Various portions of the H19 downstream enhancer may be tested individually for the ability to enhance transcription from the H19 promoter.

Alterations in the regulatory sequences can be generated using a variety of chemical and enzymatic methods which are well known to those skilled in the art. For example, regions of the sequences defined by restriction sites can be deleted. oligonucleotide-directed mutagenesis can be employed to alter the sequence in a defined way and/or to introduce restriction sites in specific regions within the sequence. Additionally, deletion mutants can be generated using DNA nucleases such as Bal31 or ExoIII and S1 nuclease. Progressively larger deletions in the regulatory sequences are generated by incubating the DNA with nucleases for increased periods of time (See Ausubel, et al., 1989 Current Protocols for Molecular Biology, for a review of mutagenesis techniques).

The altered sequences are evaluated for their ability to direct tumor specific expression of heterologous coding sequences in appropriate host cells, particularly H19-expressing carcinoma-derived cells (e.g. bladder carcinoma cells, to name an example). It is within the scope of the present invention that any altered regulatory sequences which retain their ability to direct tumor specific expression be incorporated into recombinant expression vectors for further use.

A wide variety of heterologous genes can be expressed under the control of these regulatory sequences such as genes encoding toxic gene products, potentially toxic gene products, and antiproliferation or cytostatic gene products.

Marker genes can also be expressed including enzymes, (e.g. CAT, beta-galactosidase, luciferase), fluorescent proteins such as green fluorescent protein, or antigenic markers.

Cytotoxic gene products are broadly defined to include both toxins and apoptosis-inducing agents. Additionally, for purposes of the invention, cytotoxic gene products include drug metabolizing enzymes which convert a pro-drug into a cytotoxic product. Examples of cytotoxic gene products that may be used in methods of the invention comprise diphtheria toxin, Pseudomonas toxin, ricin, cholera toxin, PE40 and tumor suppressor genes such as the retinoblastoma gene and p53. Additionally, sequences encoding apoptotic peptides that induce cell apoptosis may be used. Such apoptotic peptides include the Alzheimer's A beta peptide (see LaFerla et al., 1995, Nat. Genet. 9:21–30), the atrial natriuretic peptide (see Wu et al., 1997, J. Biol. Chem. 272:14860–14866), the calcitonin gene-related peptide (see Sakuta et al., 1996, J. Neuroimmunol. 67:103–109), as well as other apoptotic peptides known or to be discovered.

Drug metabolizing enzymes which convert a pro-drug into a cytotoxic product include thymidine kinase (from herpes simplex or varicella zoster viruses), cytosine deaminase, nitroreductase, cytochrome p-450 2B1, thymidine phosphorylase, purine nucleoside phosphorylase, alkaline phosphatase, carboxypeptidases A and G2, linamarase, β-lactamase and xanthine oxidase (see Rigg and Sikora, August 1997, Mol. Med. Today, pp. 359–366 for background).

Additionally, antisense, antigene, or aptameric oligonucleotides may be delivered to cancer cells using the presently described expression constructs. Ribozymes or single-stranded RNA can also be expressed in the cancer cell to inhibit the expression of a particular gene of interest. The target genes for these antisense or ribozyme molecules should be those encoding gene products that are essential for cell maintenance or for the maintenance of the cancerous cell phenotype. Such target genes include but are not limited to cdk2, cdk8, cdk21, cdc25A, cyclinD1, cyclinE, cyclinA and cdk4.

For example, vectors which express, under the control of regulatory sequences from imprinted genes or IGF-1 promoter that are expressed in cancer cells, antisense RNAs or ribozymes specific for the transcripts of oncogenic forms of p53, c-fos, c-jun, Kr-ras and/or Her2/neu are introduced into cells in order to down-regulate expression of the endogenous genes. Tumor cells which express H19, and can activate the H19 regulatory sequences, (or which specifically activate IGF-1, the IGF-2 P3 or P4 promoter) can be specifically targeted for expression of the antisense RNA or ribozyme RNA.

Antisense approaches involve the design of oligonucleotides (in this case, mRNA) that are complementary to the target mRNA. The antisense oligonucleotides will bind to the complementary target mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the target message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'-non-translated, non-coding regions of the target gene transcripts could be used in an antisense approach to inhibit translation of endogenous genes. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of the target mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. These studies should utilize controls that distinguish between antisense gene inhibition and nonspecific biological effects of oligonucleotides. It is also preferred that these studies compare levels of the target RNA or protein with that of an internal control RNA or protein.

Ribozyme molecules designed to catalytically cleave an essential target gene can also be used to prevent translation of target mRNA. (See, e.g., PCT International Publication WO90/11364, published Oct. 4, 1990; Sarver et al., 1990, Science 247:1222–1225). When the ribozyme is specific for a gene transcript encoding a protein essential for cancer cell growth, such ribozymes can cause reversal of a cancerous cell phenotype. While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. Construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the target mRNA; i.e., to increase efficiency and minimize the intracellular accumulation of non-functional mRNA transcripts.

Ribozymes for use in the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug et al., 1984, Science, 224:574–578; Zaug and Cech, 1986, Science, 231:470–475; Zaug et al., 1986, Nature, 324:429–433; published International Patent Application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention contemplates the use of those Cech-type ribozymes which target eight base-pair active site sequences that are present in target genes.

5.2 Activation of Genes In Tumor Cells

Cells that reactivate imprinted gene expression will also be capable of specifically activating expression constructs containing such imprinted gene regulatory regions operatively linked to a heterologous gene. Such cells, particularly tumor cells, are appropriate targets for the gene therapy methods of the invention. H19, and IGF-2 P3 and P4 specific expression in both tumors and cell lines may be determined using the techniques of RNA analysis, in situ hybridization and reporter gene constructs. In addition, tumor cells with activated IGF-1 gene expression may be similarly determined and targeted in gene therapy using the IGF-1 promoter to direct expression of a heterologous gene.

For most RNA analysis applications, a labeled probe that specifically hybridizes to the gene transcript of interest is prepared using any number of techniques well known in the art. The labeled probe can contain at least 15–30 bases complementary to the H19 nucleotide sequence, and more preferably contains at least 50 to 150 bases complementary to the H19 transcript. A particularly preferred hybridization probe for H19 expression is a polynucleotide complementary to the 3' end of the H19 message from approximately 800 base pairs upstream of the poly A site to the poly A site.

In a specific embodiment of the invention illustrated below by way of working example, a labeled antisense RNA probe is generated in vitro using a T7 or T3 expression plasmid. H19 probes can also be labeled by random priming in the presence of labeled nucleotide, for example, using the Prime-It kit (Stratagene, La Jolla, Calif.; Catalog No. 300392). Alternatively, labeled probes can be generated in a PCR reaction using a cDNA clone of the H19 coding region and primers designed to amplify a region of the coding region, or by a standard nick translation reaction.

Labels appropriate for polynucleotide probes include nucleotides incorporating radioactive isotopes (such as $^{35}S$ and $^{32}P$), fluorescent, luminescent and color tags, and enzymatic moieties.

The labeled probe is hybridized in situ to a cell or tissue sample using standard techniques such as described below by of working example, and in co-pending U.S. patent application Ser. No. 08/704,786, incorporated herein by reference. Alternatively, if a sufficient quantity of the appropriate cells can be obtained, standard RNA analysis (such as Northern analysis, RNase protection or primer extension) can be performed to determine the level of mRNA expression of the gene of interest.

Additionally, it is possible to perform such gene expression assays "in situ", i.e., directly upon tissue sections (fixed and/or frozen) of patient tissue obtained from biopsies or resections, such that no nucleic acid purification is necessary. Nucleic acid reagents such as those described above may be used as probes and/or primers for such in situ procedures (See, for example, Nuovo, G. J., 1992, "PCR In Situ Hybridization: Protocols And Applications", Raven Press, N.Y.).

An alternative method to determine if a cell type or tumor will be capable of specifically activating expression constructs containing the particular regulatory regions operatively linked to a heterologous gene is to actually transfect such expression constructs into the cell. For these purposes, the heterologous gene is preferably a marker gene product. A positive result in an assay for the marker gene product reveals that the cell or cell line is capable of activating expression from the regulatory regions.

Using these techniques, exemplary tumor types with activated H19 expression are as follows:

A. Pediatric solid tumors
 1. Wilm's tumor
 2. Hepatoblastoma
 3. Embryonal rhabdomyosarcoma
B. Germ cell tumors and trophoblastic tumors
 1. Testicular germ cell tumors
 2. Immature teratoma of ovary
 3. Sacrococcygeal tumor
 4. Choriocarcinoma
 5. Placental site trophoblastic tumors
C. Epithelial adult tumors
 1. Bladder carcinoma
 2. Hepatocellular carcinoma
 3. Ovarian carcinoma
 4. Cervical carcinoma
 5. Lung carcinoma
 6. Breast carcinoma
 7. Squamous cell carcinoma in head and neck
 8. Esophageal carcinoma
 9. Thyroid carcinoma
D. Neurogenic tumors
 1. Astrocytoma
 2. Ganglioblastoma
 3. Neuroblastoma Accordingly, the above cancers are treatable by the methods of the invention. In fact, any tumors which activate H19 expression may be treated by the methods of the invention.

Additionally, the aforementioned techniques may be applied to determine tumors that activate the IGF-1, and the IGF-2 P3 and P4 promoters. Such tumors are also treatable by the methods of the invention. For example, IGF-2 is activated in childhood tumors, such as Wilm's tumors, rhabdomyosarcomas, neuroblastomas and hepatoblastomas.

5.3 Methods Of Introducing Polynucleotides Under The Control Of Regulatory Sequences Into Host Cells The invention also pertains to a host cell transfected with polynucleotides containing regulatory regions operatively linked to a heterologous gene. Such host cells may be maintained in culture or may be part of an animal, preferably a mammal. Polynucleotides of interest are typically inserted into any of a wide range of vectors which are subsequently delivered using the presently disclosed methods and materials. Such vectors can be produced using well established molecular biology techniques (see generally, Sambrook et al. (1989) *Molecular Cloning* Vols. I–III, Cold Spring Harbor Laboratory Press, Cold Spring Harbor, N.Y., and *Current Protocols in Molecular Biology* (1989) John Wiley & Sons, all Vols. and periodic updates thereof, herein incorporated by reference). Typically, where translation is desired, the heterologous genes of interest will also be engineered to comprise a suitable 3' polyadenylation sequence if necessary.

5.3.1 Cultured Cells

Host cells transfected with polynucleotides containing imprinted gene regulatory regions operatively linked to a heterologous gene may be any prokaryotic or eukaryotic cell. Ligating the polynucleotide into a gene construct, such as a vector, and transforming or transfecting into host cells, either eukaryotic (yeast, avian, insect or mammalian) or prokaryotic (bacterial cells) are standard procedures used widely in the microbial or tissue-culture technologies.

Vectors suitable for cultivation of the subject polynucleotides in bacterial cells, such as *E. coli*, include plasmids of the types: pBR322-derived plasmids, pEMBL-derived plasmids, pEX-derived plasmids, pBTac-derived plasmids, and pUC-derived plasmids. For replication in yeast, the YEP24, YIP5, YEP51, pYES2 and YRP17 plasmids are cloning and expression vehicles useful in the introduction of genetic constructs in *S. cerevisiae* (see, for example, Broach et al., 1993, in *Experimental Manipulation of Gene Expression*, ed. M. Inouye, Academic press, p. 83). These vectors can replicate in both *E. coli* due to the presence of the pBR322 ori, and in yeast due to the replication determinant of the yeast 2 µm circle plasmid. In addition, drug resistant markers such as ampicillin can be used.

Similarly, preferred mammalian vectors for the polynucleotides of the invention contain both prokaryotic sequences to facilitate the propagation of the vector in bacteria. Such vectors, when transfected into mammalian cells, can be designed to integrate into the mammalian chromosome for long term stability by use of a linked selectable marker gene. Alternatively, derivatives of viruses such as the bovine papillomavirus (BPV-1) or Epstein-Barr virus can be used for transient expression. The various methods employed in the preparation of plasmid transformation of host organisms are well known in the art. For other suitable vector systems, as well as general recombinant procedures, see Sambrook et al., supra.

5.3.2 Gene Therapy

The invention also encompasses the use of polynucleotides containing a gene regulatory region operatively linked to a heterologous gene for use in gene therapy to treat cancer and hyperproliferative diseases. For gene therapy purposes, expression constructs of the instant invention may be administered in any biologically effective carrier, e.g., any formulation or composition capable of effectively delivering the recombinant gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example cationic polymers, cationic liposomes (e.g. lipofectin, cholesterol derivatives such as D.D.A.B. and cationic phospholipids) or derivatized (e.g., antibody conjugated), polylysine conjugates, gramicidin S, artificial viral envelopes or other such intracellular carriers, as well as direct injection of the naked gene construct, electroporation or CaPO$_4$ precipitation carried out in vivo. A recent review of gene transfer and expression systems for cancer gene therapy is Cooper, 1996, Seminars in Oncology 23:172–187.

It will be appreciated that because transduction of appropriate target cells represents an important first step in gene therapy, choice of the particular gene delivery system will depend on such factors as the phenotype of the intended target and the route of administration, e.g. locally or systemically. Furthermore, it will be recognized that the particular gene construct provided for in vivo transduction of expression constructs are also useful for in vitro transduction of cells, such as for use in the ex vivo tissue culture systems described above.

A preferred approach for in vivo introduction of nucleic acid into a cell is by use of a viral vector containing nucleic acid, e.g., a particular cytotoxic gene under the control of H19 regulatory sequences. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. Suitable vectors which can be delivered using the presently disclosed methods and compositions include, but are not limited to, herpes simplex virus vectors, adenovirus vectors, adeno-associated virus vectors, retroviral vectors, pseudorabies virus, alpha-herpes virus vectors, and the like. A thorough review of viral vectors, particularly viral vectors suitable for modifying nonreplicating cells, and how to use such vectors in conjunction with the expression of polynucleotides of interest can be found in the book "Viral Vectors: Gene Therapy and Neuroscience Applications" Ed. Caplitt and Loewy, Academic Press, San Diego (1995).

It has been shown that it is possible to limit the infection spectrum of viruses and consequently of viral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al., 1989, Proc. Nat. Acad. Sci. USA 86:9079–9083; Julan et al., 1992, J. Gen. Virol. u3:3251–3255; and Goud et al., 1983, Virology 163:251–254); or coupling cell surface receptor ligands to the viral env proteins (Neda et al., 1991, J. Biol. Chem 266:14143–14146). Coupling can be in the form of the chemical cross-linking with a protein or other variety (e.g. lactose to convert the env protein to an asialogycoprotein), as well as by generating fusion proteins (e.g. single-chain antibody/env fusion proteins). For example, cancer cells may be targeted using this technique by, for example, coupling antibodies against tumor-associated molecules or cancer cell surface proteins to the surface of the recombinant virus. This technique, while useful to limit or otherwise direct the infection to certain tissue types, can also be used to convert an ectotropic vector into an amphotropic vector.

A preferred viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al., 1988, BioTechniques 6:616; Rosenfeld et al., 1991, Science 252:431–434; and Rosenfeld et al., 1992, Cell 68:143–155. Suitable adenoviral vectors derived from the adenovirus strain AD type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al., 1992, cited supra), endothelial cells (Lemarchand et al., 1992, Proc. Natl. Acad Sci. USA 89:6482–6486), hepatocytes (Herz and Gerard, 1993, Proc. Natl. Acad. Sci USA 90:2812–2816) and muscle cells (Quantin et al., 1992, Proc. Natl. Acad. Sci USA 89:2581–2584). Furthermore, the virus particle is relatively stable, amenable to purification and concentration, and can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., cited supra, Haj-Ahmand and Graham, 1986, J. Virol. 57:267). Most replication-defective adenoviral vectors currently in use and therefore favored by the present invention are deleted for all or part of the viral E1 and E3 genes but retain as much as 80% of the adenoviral genetic material (see, e.g., Jones et al., 1979, Cell 16:683; Berkner et al., supra; and Graham et al. in Methods in Molecular Biology, E. J. Murray, Ed. (Humana, Clifton N.J., 1991) vol. 7, pp. 109–127).

Another viral vector system useful for delivery of one of the subject expression constructs is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., 1992, Curr. Topics in Micro. and Immunol. 158:97–129). It is also one of the few viruses that may integrate its DNA into non-dividing cells, and exhibits a high frequency of stable interaction (see for example Flotte et al., 1992, Am. J. Respir. Cell. Mol. Biol. 7:349–354; Samulski et al., 1989, J. Virol. 63:3822–3828; and McLaughlin et al., 1989, J. Virol. 63:1963–1973). Vectors containing as little as 300 base pairs of AAV can be packaged and can integrate. Space for exogenous DNA is limited to about 4.5 kb. An AAV vector such as that described in Tratschin et al., 1985, Mol. Cell. Biol. 5:3251–3260 can be used to introduce DNA into cells. A variety of nucleic acids have been introduced into different cell types using AAV vectors (see for example Hermonat et al., 1984, Proc. Natl. Acad. Sci USA 81:6466–6470; Tratschin et al., 1985, Mol. Cell. Biol. 4:2072–2081; Wondisford et al., 1988, Mol. Endocrinol. 2:32–39; Tratschin et al., 1984, J. Virol. 51:611–619; and Flotte et al., 1993, J. Biol. Chem. 268:3781–3790).

In addition to viral transfer methods, such as those illustrated above, non-viral methods can also be employed to cause directed expression of a desired heterologous gene in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject expression constructs by the targeted cell. Exemplary gene delivery systems of this type include liposomal derived systems, poly-lysine conjugates, and artificial viral envelopes.

In clinical settings, the gene delivery systems for the therapeutic expression construct can be introduced into a patient by any of a number of methods, each of which is well known in the art. For instance, a pharmaceutical preparation of the gene delivery system can be introduced systemically, e.g. by intravenous injection, and specific expression of the construct in the target cells occurs predominantly from specificity of transfection provided by cell-type or tissue-type expression due to the regulatory sequences controlling expression of the heterologous gene, or the regulatory sequences in combination with the gene delivery vehicle targeting particular cell types. In other embodiments, initial delivery of the recombinant expression construct is more limited with introduction into the animal being quite localized. For example, the gene delivery vehicle can be introduced by catheter (see U.S. Pat. No. 5,328,470) or by stereotactic injection (e.g. Chen et al., 1994, Proc. Nat. Acad. Sci. USA 91:3054–3057). An expression construct of the invention can be delivered in a gene therapy construct by electroporation using techniques described, for example, by Dev et al., 1994, Cancer Treat. Rev. 20:105–115.

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells which produce the gene delivery system.

5.3.3 Therapeutic Endpoints and Dosages

One of ordinary skill will appreciate that, from a medical practitioner's or patient's perspective, virtually any alleviation or prevention of an undesirable symptom associated with a cancerous condition (e.g., pain, sensitivity, weight loss, and the like) would be desirable. Additionally, any reduction in tumor mass or growth rate is desirable, as well as an improvement in the histopathological picture of the tumor. Thus, for the purposes of this Application, the terms "treatment", "therapeutic use", or "medicinal use" used herein shall refer to any and all uses of the claimed compositions which remedy a disease state or symptoms, or otherwise prevent, hinder, retard, or reverse the progression of disease or other undesirable symptoms in any way whatsoever.

An effective dosage and treatment protocol may be determined by conventional means, starting with a low dose in laboratory animals and then increasing the dosage while monitoring the effects, and systematically varying the dosage regimen as well. Animal studies, preferably mammalian studies, are commonly used to determine the maximal tolerable dose, or MTD, of bioactive agent per kilogram weight. Those skilled in the art regularly extrapolate doses for efficacy and avoiding toxicity to other species, including human.

Before human studies of efficacy are undertaken, Phase I clinical studies in normal subjects help establish safe doses. Numerous factors may be taken into consideration by a clinician when determining an optimal dosage for a given subject. Primary among these is the toxicity and half-life of the chosen heterologous gene product. Additional factors include the size of the patient, the age of the patient, the general condition of the patient, the particular cancerous disease being treated, the severity of the disease, the presence of other drugs in the patient, the in vivo activity of the gene product, and the like. The trial dosages would be chosen after consideration of the results of animal studies and the clinical literature.

For example, a typical human dose of an adenoviral vector containing an H19 regulatory region operatively linked to a heterologous gene encoding a cytotoxic agent such as thymidine kinase is from $1 \times 10^7$ pfu to $1 \times 10^{10}$ pfu injected directly into the tumor mass per day. More preferably, the daily dose of such an adenoviral vector injected directly into a tumor would be from $1 \times 10^8$ pfu to $1 \times 10^{10}$ pfu, depending upon the tumor size. For an adenoviral vector containing an H19 regulatory region operatively linked to a cytotoxic gene product with a different level of toxicity, these values would of course be altered accordingly. Similar doses of an adenoviral vector containing an IGF-2 P4 promoter operatively linked to a heterologous gene encoding a cytotoxic agent such as thymidine kinase can also be used as a suggested starting point.

Particularly where in vivo use is contemplated, the various biochemical components of the present invention are preferably of high purity and are substantially free of potentially harmful contaminants (e.g., at least National Food (NF) grade, generally at least analytical grade, and preferably at least pharmaceutical grade). To the extent that a given compound must be synthesized prior to use, such synthesis or subsequent purification shall preferably result in a product that is substantially free of any potentially toxic agents which may have been used during the synthesis or purification procedures.

For use in treating a cancerous condition in a subject, the present invention also provides in one of its aspects a kit or package, in the form of a sterile-filled vial or ampoule, that contains a polynucleotide vector containing an H19 regulatory region operatively linked to a heterologous gene encoding a cytotoxic agent or a vector-releasing cell. In one embodiment, the kit contains a polynucleotide vector containing an H19 regulatory region operatively linked to a heterologous gene encoding a cytotoxic agent, as an administration-ready formulation, in either unit dose or multi-dose amounts, wherein the package incorporates a label instructing use of its contents for the treatment of cancer. Alternatively, and according to another embodiment of the invention, the package provides a sterile-filled vial or ampoule containing such a vector-releasing cell or cell line. For storage and transport, the vector-releasing cell or cell line should be frozen. optionally, the package may also contain media and reagents for culturing the vector-releasing cell or cell line.

The invention having been described, the following examples are offered by way of illustration and not limitation.

6. EXAMPLE

H19 Regulatory Sequences Facilitate Expression of a Heterologous Gene in Tumor Cell Lines This section describes the construction of a variety of expression constructs containing a CAT reporter gene placed under the control of H19 regulatory sequences and their transfer into several different bladder cancer cell lines.

6.1 Materials and Methods 6.1.1 Cell Lines and Transfections

Bladder cancer cell lines HT-1376, EJ28, T24P, 1197 and UM-UC-3 were obtained from the American Type Culture Collection (ATCC) and maintained according to ATCC recommendations.

Transient transfections were carried out using the calcium phosphate precipitation transfection method. Precipitants (containing 7 µg plasmid) were added in 1 ml of media to $0.3 \times 10^6$ cells in 30 mm dishes. After 16 hours, transfection media was removed and fresh media added. Cells were harvested 24–96 hours after transfection and CAT activity determined using the butyryl-CoA organic phase extraction procedure (Sambrook et al., 1989). An aliquot of the organic upper phase (100 µl) was transferred to a scintillation well containing 3 ml of scintillation fluid and counted.

6.1.2 Construction of Expression Vectors

Plasmids pCAT-basic (containing a CAT reporter gene preceded by a multiple cloning site), pCAT-promoter (containing the CAT reporter gene under the control of an SV40 promoter), pCAT-enhancer (containing the SV40 enhancer downstream of the CAT reporter gene, and a multiple cloning site for insertion of a promoter upstream of the CAT reporter gene) and pCAT-control (containing the CAT reporter gene under control of both the SV40 promoter and enhancer) were all obtained commercially from Promega (Madison, Wis.).

To construct the plasmid pH19E, containing the CAT reporter gene under the control of the H19 promoter, the H19 promoter region (SEQ ID NO:1) was first cloned into pBluescript II SK+ (Promega). A polynucleotide containing the H19 promoter sequence was amplified from human placenta DNA using primers ESPCR21: CGGTTCCCCACTTCCCCAGTTT (SEQ ID NO:6) and ESPCR22: CGGAAGTCGACAACCCTCACCAAAGGC-CAAGGT (SEQ ID NO:7). The PCR product was end-polished with Klenow enzyme and cloned into the EcoRV site of pBluescriptIISK+. The inserted DNA was verified by digestion with the internally cutting enzymes PvuII, EcoRI and ApaI. The orientation of the promoter was opposite that of the lacZ coding region of the vector. The promoter region was then excised by cleavage with HindIII and PstI, and the resulting approximately 0.9 kb fragment was inserted into the HindIII-PstI sites of pCAT-basic to produce pH19E.

Expression plasmids containing the H19 enhancer region inserted in both orientations downstream of the H19 promoter/CAT reporter gene were constructed as follows. A 5 kb SacI fragment containing the H19 downstream enhancer (from +6.0 kb to +11 kb relative to the start of H19 transcription) was cloned into the SacI site of pUC19. This enhancer fragment was then excised with EcoRI and HindIII and ligated into the EcoRI-HindIII sites of pBluescript II SK+ to create pBhH19En-Sa. pBhH19En-Sa was partially digested with BamHI, and the 5 kb fragment containing the H19 enhancer (and an internal BamHI site) was cloned into the BamHI site downstream of the H19 promoter/CAT reporter gene in pH19E. Plasmids containing the H19 enhancer in both the direct (pH19EH19D) and reverse (pH19EH19R) orientations were generated.

6.2 Results and Discussion

Five different bladder cancer cell lines HT-1376, EJ28, T24P, 1197 and UM-UC-3 were each transfected with pCAT-basic (designated P-E in FIG. 2), pCAT-control (designated pSV40ESV40 in FIG. 2), pH19E, pH19EH19D and pH19 EH19R. The expression results of each construct are presented in FIGS. 3A–3E. In each cell line, the highest level of CAT activity was observed with the pCAT-control plasmid containing both the SV40 enhancer and SV40 promoter. This construct served as a positive control, as SV40 regulatory sequences have been established as inducers of gene expression. However, SV40 regulatory sequences are not tumor cell-specific in their ability to induce gene expression. Cell lines transfected with pH19E, containing the CAT reporter gene under the control of the H19 promoter, also exhibited significantly increased expression of CAT over background. The level of induction of CAT activity by the H19 promoter ranged from five fold in the HT-1376 cell line to ten fold in the UM-UC-3 cell line. Addition of the H19 enhancer to the H19 promoter/CAT reporter gene constructs further increased levels of expression in certain cell lines. For example, in cell lines EJ28, T24P and 119, the H19 enhancer significantly increased expression from the H19 promoter/CAT reporter gene. However, the orientation of the enhancer gave different results in different cell lines. In cell lines HT1376 and UM-UC-3, the enhancer had little or no effect on expression.

The results demonstrate that the human H19 promoter region directs the expression of an operatively linked heterologous reporter gene in a wide variety of bladder cancer-derived cell lines. In some bladder cancer-derived cell lines, the H19 enhancer can further increase expression of a reporter gene under the control of H19.

7. EXAMPLE

A Toxin Gene Under The Control Of H19 Regulatory Sequences 7.1 Materials and Methods The expression constructs described above in Section 6 are modified to express a sequence encoding a toxic product or a prodrug instead of CAT. For example, the sequence encoding the CAT gene product is removed and replaced with a sequence encoding herpes simplex virus thymidine kinase (HSV-TK) using standard cloning methods that are well known in the art.

The H19 /prodrug expression plasmids are transfected into bladder cancer-derived cell lines as described in Section 6. When transfected into bladder cancer cell lines, an H19 /HSV-TK expression plasmid induces bladder cancer cell specific cytotoxicity in the presence of ganciclovir.

8. EXAMPLE

Expression Of H19 In A Mouse Model Of Chemically Induced Bladder Carcinoma 8.1 Materials and Methods Seventy five-week old female C3H/He mice (Charles River) were housed at 6 mice per cage and allowed to acclimatize in an air-conditioned room with a 12 hour light/12 hour dark cycle. At 8 weeks of age, the experiment was begun and the mice divided arbitrarily into a control group (10 mice) and experimental group (60 mice). The experimental group of mice were given 0.05% N-butyl-N-(4-hydroxybutyl)nitrosamine (BBM) (Tokyo Kasei Kogyo Co. Ltd., Tokyo, Japan) dissolved in their drinking water ad libitum. Control mice were given tap water. Animals from both groups were killed at 4, 8, 12, 16, 20 and 26 weeks after the start of the experiment. The bladders were excised, fixed, and embedded in paraffin blocks using standard procedures.

8.1.1 Preparation of Probe

A 2.1 kb fragment containing the mouse H19 coding region was subcloned into the pBluescript II KS plasmid (Stratagene, La Jolla, Calif.) behind the T7 and T3 RNA polymerase binding sites. [$^{35}$S]-labeled antisense H19 RNA was produced in vitro from HindIII-linearized plasmid DNA using T7 polymerase (Boehringer Mannheim) and an Amersham RPN 2006 kit. In vitro-generated transcripts had a specific activity of $10^7$ cpm/µg. Sense H19 mRNA, prepared with T3 polymerase (Boehringer Mannheim) and EcoRI-linearized template, was used as a control.

8.1.2 In situ Hybridization

Paraffin wax sections (5 µM) of formalin fixed tissues were mounted on 3-aminopropyltriethoxylane (Tespa, Sigma) coated microscope slides and dried overnight at 37° C. Sections were dewaxed with xylene, fixed with 4% paraformaldehyde, and then treated with proteinase K (Sigma). Slides were acetylated to reduce non-specific binding of the probe and dehydrated through an ethanol series. [$^{35}$S]-labeled RNA probes (specific activity of 50,000 cpu/µl) were hybridized as described by Rangini et al., 1991, Mech. Dev. 35:13–24, omitting the thio-AMP step. Slides were exposed to film for 10 days, and counter-stained with hematoxylin and eosin. The slides were examined and photographed using a Polyvar (Reichert Jung) microscope under bright and dark field illumination. Controls included hybridization with sense RNA probe and RNAse prehybridization treatment. Additionally, sections of bladders from adult healthy mice (which do not express H19) and embryonal mouse bladders (which do express H19) served as negative and positive controls, respectively.

8.2 Results and Discussion

By 26 weeks, all of the surviving experimental group mice had developed palpable bladder tumors. Extensive expression of H19 was observed in the chemically induced bladder tumors. In contrast, no expression of H19 was detected in normal adult bladder. Accordingly, this mouse model of chemically induced bladder cancer may be used as an animal model to demonstrate the tumor-specific cytotoxicity in vivo of constructs containing the H19 regulatory regions operatively linked to a toxin gene.

9. EXAMPLE

Gene Therapy Using H19 Regulatory Sequences To Express A Heterologous Gene In A Mouse Model of Bladder Carcinoma The H19 /toxin or prodrug expression plasmids are incorporated into liposomes (as described by Takashita et al., 1993, J. Clin. Invest. 93:652–651, incorporated herein by reference) for delivery to mouse bladder in vivo. Mice used for this experiment have chemically induced bladder tumors as described above in Section 8.

Briefly, 50 µg of plasmid DNA, dissolved in 500 µl of Optimen's serum-free medium (BRL Life Technologies, Gaithersburg, Md.) is added to 250 µl of Lipofectamine™ (BRL Life Technologies) previously dissolved in 250 µl of water. The mixture is incubated for 30 minutes at room temperature, then diluted in 10 mls of balanced salt solution (BSS(−): 140 mM NaCl, 5.4 mM KCl, 10 mM Tris-HCl, pH 7.6). After pelleting by centrifuging the solution at 15,000 rpm for 30 minutes, the liposomes are resuspended in 1 ml of BSS(−) containing 1 mM $CaCl_2$. Approximately 0.2 mls of the concentrated liposomes are administered to mice that have chemically induced bladder tumors via catheter. A control group of mice with bladder tumors receive liposomes with no DNA or with a construct containing an irrelevant gene under the control of the H19 regulatory sequences. At defined timepoints, mice from each group are sacrificed and the bladders excised, fixed, and embedded in paraffin blocks using standard procedures. Alternate sections are processed for in situ hybridization using either the H19 probe, as described above, or a probe to the coding sequence of Pseudomonas toxin gene. Additionally, the size, number, and necrosis of tumors are compared between the control and experimental groups. Expression of Pseudomonas toxin is found to co-localize with expression of H19 in the bladder tumors from the experimental group of mice. Additionally, the bladder tumors in the experimental group of mice are reduced in size and necrotic as compared to the bladder tumors in the control group of mice.

10. EXAMPLE

Expression from the IGF-2 P3 and P4 Promoters in Tumor Cell Lines 10.1 Materials and Methods In this experiment, a variety of expression constructs containing the luciferase reporter gene placed under the control of one of the four different IGF-2 promoters were constructed and transferred into several different bladder cancer cell lines. The following human IGF-2 promoter/luciferase constructs were made:

| Plasmid Construct | IGF-2 Gene Nucleotide Sequence | Promoter |
| --- | --- | --- |
| Hup1 | −980 to +54 | Promoter 1 |
| Hup2 | −379 to +271 | Promoter 2 |
| Hup3 | −1229 to +140 | Promoter 3 |
| Hup4 | −546 to +102 | Promoter 4 |

The IGF-2 promoter sequences are described in Sussenbach et al., 1992, Growth Reg. 2:1–9, incorporated herein by reference. The luciferase reporter vector is commercially available from Promega, Madison, Wis. (catalog #E1641).

10.2 Results and Discussion

The resulting expression plasmids were transfected into human bladder cancer cell lines HT-1376, EJ28, T24P, 1197 and UM-UC-3 as described above in Section 6. Luciferase activity was assayed using a commercial kit (Promega, Madison, Wis., catalog #E1500). The results, shown in FIGS. 4A–4E, demonstrate that the IGF-2 P4 promoter directed the expression of the luciferase reporter gene in each bladder cancer cell line tested. In cell line 1197, the IGF-2 P3 promoter also directed the expression of the luciferase reporter gene. In subsequent experiments, IGF-2 P3 and P4 promoters were shown to direct expression of luciferase gene expression in other tumor cell lines, including choriocarcinoma cells and rhabdomyosarcoma cells.

11. EXAMPLE

H19 Promoter and IGF-2 Promoter Function with H19 Enhancer to Facilitate Expression of a Heterologous Gene 11.1 Materials and Methods Four luciferase reporter vectors, pGL3-Basic, pGL3-Promoter, pGL3-Enhancer and pGL3-Control were obtained from Promega. These vectors were transfected into cultured cell lines using a number of different transfection reagents, including lipofetamine (Gibco/BRL), fugene (Boehringer), the Perfect Transfection Kit of 8 different lipids reagents (Invitrogen), TFX-10, TFX-20, transfast (Promega), and the calcium phosphate method (Gorman et al., 1982, Mol. Cell. Biol. 2:1044–1051).

The H19 promoter cloned into EcoRV site of pBluescript II SK (pbh19p #1) is described in Section 6.1, supra. The H19 promoter was excised by cleavage with Sma I and Hind III, and the resulting 0.9 kb fragment was inserted into the Sma I-Hind III sites of pGL3-Basic vector to produce the Lucp-bh19 construct.

The H19 promoter region from nt −819 to +14 was amplified by PCR from the pbh19p #1 plasmid, using primers 5'-ATATGGTACCGACAACCCTCACCAAAG-3' (upstream, SEQ ID NO:8) and 5'-ATATAAGCTTCTTCTCCCTCACCCTGCTC-3' (downstream, SEQ ID NO:9). The resulting PCR product was digested with KpnI and Hind III, and ligated into the KpnI-Hind III sites of pGL3-Basic vector, yielding the Luc-PBH19 construct. This PCR-generated H19 promoter was sequenced on both direction by automated dye terminator cycle sequencing (ABT Prism 377 DNA sequencer, Perkin Elmer). FIG. 5 shows the nucleotide sequence of the H19 promoter (SEQ ID:NO 2) generated by PCR.

The 5 kb H19 downstream enhancer described in Section 6, supra, was digested with DamH to yield two fragments of 4.1 kb and 0.9 kb at the 3' end. The Luc-PBH19-0.9EH19 and Luc-PBH19-4EH19 constructs were constructed by the insertion of the 0.9 kb and 4.1 kb BamH I fragments of the H19 enhancer into the BamH I site of Luc-PBH19 plasmid, respectively. The enhancer sequences were positioned downstream of the H19 promoter/luciferase reporter gene.

The BamH I enhancer fragment of 0.9 kb was ligated into the BamH I site of pGL-Basic vector to produce the Luc-0.9EH19 vector. The H19 promoter of the pbh19p #1 plasmid was excised by KpnI-BamH I, and ligated into the KpnI-BglII sites of the Luc-0.9EH19 construct, yielding the Luc-pbh190-0.9EH19 expression construct which contained the promoter clones as described in Section 6, supra, and the 0.9 kb enhancer downstream of the H19 /Luc reporter gene.

Expression vectors designated as Hup-1, Hup-2, Hup-3, and Hup-4, containing the luciferase gene under the control of the human IGF-2 promoters P1,P2, P3 and P4, respectively, were constructed as described in Sussenbach et al., 1992, Growth Reg. 2:1–9. A 512 bp region of P4 was amplified by PCR from the Hup-4 construct using primers 5'ACAGGTACCTCTAGAGTCGACCT-3' (upstream, SEQ ID NO:10) and 5'-ATATAAGCTTGCTCCCATCCTGCA-3' (downstream, SEQ ID NO:11). The resulting PCR product was digested with KpnI-Hind III, and ligated into the KpnI-Hind III sites of the reporter gene vector pGL3-Basic to produce the Luc-P4 reporter gene vector.

Expression vectors containing the IGF-2 P4 promoter and the H19 enhancer were also prepared. A BamHI enhancer fragment of 2 kb derived from the 4.1 kb fragment previously described was cloned into the BamH I site of the Luc-P4 construct, producing the Luc-P4-2 EH19 expression vector.

The 0.9 kb, 2 kb and 4.1 kb H19 enhancers were sequenced using automated DNA sequencing. The nucleotide sequence of the 0.9 kb enhancer is shown in FIG. 6 (SEQ ID NO:3). The nucleotide sequence of the 2 kb enhancer is shown in FIGS. 7A and 7B (SEQ ID NO:4). The nucleotide sequence of the 4.1 kb enhancer is shown in FIGS. 8A–8C (SEQ ID NO:5).

11.2 Results and Discussion

When several transfection reagents were used to introduce four luciferase gene-containing vectors into cultured cell lines, calcium phosphate precipitation produced the highest transfection efficiency for most of the cell lines tested. Therefore, calcium precipitation was subsequently used to transfect various expression vectors. In addition, increased concentration of plasmid DNA did not inhibit transfection efficiency, even when they used at concentrations above the plateau.

The bladder cancer cell line 5637, the hepatocellular carcinoma (HCC) cell line Huh7 and the kidney tumor cell line 293T were each transfected with different constructs containing the luciferase reporter gene under the control of the H19 or IGF-2 P4 promoter in combination with the H19 enhancer.

Cells transfected with Luc-ph19 and Luc-PH19 containing the reporter gene and the H19 promoter exhibited increased gene expression over the background (FIGS. 9A–9C). The construct Luc-PH19 containing the PCR-generated promoter shows a higher activity than the Luc-ph19 in each cell line tested. Addition of the H19 0.9 kb enhancer fragment to the Luc-ph19 reporter vector (Luc-ph19-0.9EH19) further increased levels of expression from 2 to 4 folds in the cell lines 5637 and 293T, respectively.

The IGF-2 P4 promoter also increased the expression of luciferase in all cell lines over background. Addition of the 2 kb H19 enhancer fragment to the Luc-P4 expression vector enhanced the P4 promoter activity. The level of induction of luciferase activity by the 2 kb enhancer fragment ranged from two fold in 293T cell line to six fold in the Huh7 cell line, while the enhancer only marginally enhanced the promoter activity in 5673 cells.

FIGS. 10A–10E shows that expression of the construct Luc-ph19-4EH19) containing both the PCR-generated H19 promoter and 4.1 kb H19 enhancer fragment. The enhancer greatly increased the activity of the promoter by 3–28 folds in the cell lines except in the 5637 cell line.

12 DEPOSIT OF CLONE

The following plasmid was deposited with the American Type Culture Collection (ATCC), Manassas, Va., under the terms of the Budapest Treaty on the International Recognition of the Deposit of Microorganisms for Purposes of Patent Procedure:

| Clone | ATCC Access. No. | Date of Deposit |
|---|---|---|
| pH19EH19 | 209322 | October 2, 1997 |

EQUIVALENTS

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims.

All publications cited herein are incorporated by reference in their entirety.

What is claimed is:

1. A method of treating cancer in a subject comprising administering, into a tumor of a subject, a polynucleotide encoding a cytotoxic gene product operably linked to a regulatory sequence, wherein the regulatory sequence is derived from an H19, IGF-1, or IGF-2 P4 promoter regulatory element.

2. The method of claim 1 wherein the regulatory sequence is an H19 regulatory sequence.

3. The method of claim 1 or 2 wherein the cytotoxic gene product is selected from the group consisting of diphtheria toxin, pseudomonas toxin, ricin, cholera toxin or retinoblastoma gene.

4. The method of claim 2, wherein the H19 regulatory sequence is an H19 promoter, an H19 enhancer, or both an H19 promoter and an H19 enhancer.

5. The method of claim 4, wherein the H19 promoter comprises nucleotide 1 through 830 or SEQ ID NO: 1.

6. The method of claim 4, wherein the H19 promoter comprises the sequence of SEQ ID NO: 2.

7. The method of claim 4, wherein the H19 enhancer comprises the sequence of the H19 enhancer cloned in plasmid pH19EH19 (ATCC deposit no. 209322).

8. The method of claim 4, wherein the H19 enhancer comprises the sequence of SEQ ID NO: 3.

9. The method of claim 4, wherein the H19 enhancer comprises the sequence of SEQ ID NO: 4.

10. The method of claim 4, wherein the H19 enhancer comprises the sequence of SEQ ID NO: 5.

11. The method of claim 4, wherein the enhancer is placed 3' to the heterologous sequence encoding the cytostatic or cytotoxic gene product.

12. The method of claim 4, wherein the cancer is selected from bladder carcinoma, hepatocellular carcinoma, hepatoblastoma, rhablomyosarcoma, ovarian carcinoma, cervical carcinoma, lung carcinoma, breast carcinoma, squamous cell carcinoma, thyroid carcinoma, ostrocytoma, ganglio blastoma and neuroblastoma.

* * * * *

SEQUENCE LISTING

<160> NUMBER OF SEQ ID NOS: 11

<210> SEQ ID NO 1
<211> LENGTH: 830
<212> TYPE: DNA
<213> ORGANISM: Homo Sapien

<400> SEQUENCE: 1

| | | | | | |
|---|---|---|---|---|---|
| ctgcagggcc | ccaacaaccc | tcaccaaagg | ccaaggtggt | gaccgacgga | cccacagcgg | 60 |
| ggtggctggg | ggagtcgaaa | ctcgccagtc | tccactccac | tcccaaccgt | ggtgccccac | 120 |
| gcgggcctgg | gagagtctgt | gaggccgccc | accgcttgtc | agtagagtgc | gcccgcgagc | 180 |
| cgtaagcaca | gcccggcaac | atgcggtctt | cagacaggaa | agtggccgcg | aatgggaccg | 240 |
| gggtgcccag | cggctgtggg | gactctgtcc | tgcggaaacc | gcggtgacga | gcacaagctc | 300 |
| ggtcaactgg | atgggaatcg | gcctgggggg | ctggcaccgc | gcccaccagg | gggtttgcgg | 360 |
| cacttccctc | tgcccctcag | caccccaccc | ctactctcca | ggaacgtgag | gtctgagccg | 420 |
| tgatggtggc | aggaaggggc | cctctgtgcc | atccgagtcc | ccagggaccc | gcagctggcc | 480 |
| cccagccatg | tgcaaagtat | gtgcaggcg | ctggcaggca | gggagcagca | ggcatggtgt | 540 |
| cccctgaggg | gagacagtgg | tctgggaggg | agaggtcctg | gaccctgagg | gaggtgatgg | 600 |
| ggcaatgctc | agccctgtct | ccggatgcca | aggagggt | gcgggaggc | cgtctttgga | 660 |
| gaattccagg | atgggtgctg | ggtgagagag | acgtgtgctg | gaactgtcca | gggcggaggt | 720 |
| gggccctgcg | ggggccctcg | ggagggccct | gctctgattg | gccggcaggg | cagggcggg | 780 |
| aattctggcg | ggccacccca | gttagaaaaa | gcccgggcta | ggaccgagga | | 830 |

<210> SEQ ID NO 2
<211> LENGTH: 833
<212> TYPE: DNA
<213> ORGANISM: Homo Sapien

<400> SEQUENCE: 2

| | | | | | |
|---|---|---|---|---|---|
| gacaaccctc | accaagggcc | aaggtggtga | ccgacggacc | cacagcgggg | tggctggggg | 60 |
| agtcgaaact | cgccagtctc | cactccactc | ccaaccgtgg | tgccccacgc | gggcctggga | 120 |
| gagtctgtga | ggccgcccac | cgcttgtcag | tagagtgcgc | ccgcgagccg | taagcacagc | 180 |
| ccggcaacat | gcggtcttca | gacaggaaag | tggccgcgaa | tgggaccggg | gtgcccagcg | 240 |
| gctgtgggga | ctctgtcctg | cggaaaccgc | ggtgacgagc | acaagctcgg | tcaactggat | 300 |
| gggaatcggc | tgggggct | ggcaccgcgc | ccaccagggg | gtttgcggca | cttccctctg | 360 |
| cccctcagca | ccccaccct | actctccagg | aacgtgagtt | ctgagccgtg | atggtggcag | 420 |
| gaagggcc | tctgtgccat | ccgagtcccc | agggacccgc | agctggcccc | cagccatgtg | 480 |
| caaagtatgt | gcaggcgct | ggcaggcagg | agcagcagg | catggtgtcc | cctgagggga | 540 |
| gacagtggtc | tgggagggag | aagtcctggc | cctgaggag | gtgatgggc | aatgctcagc | 600 |
| cctgtctccg | gatgccaaag | gagggtgcg | ggaggccgt | ctttggagaa | ttccaggatg | 660 |
| ggtgctgggt | gagagagacg | tgtgctgaa | ctgtccaggg | cggaggtggg | ccctgcgggg | 720 |
| gccctcggga | gggccctgct | ctgattggcc | ggcagggcag | gggcgggaat | ctgggcggg | 780 |
| gccacccag | ttagaaaaag | cccgggctag | gaccgaggag | cagggtgagg | gag | 833 |

<210> SEQ ID NO 3
<211> LENGTH: 877
<212> TYPE: DNA
<213> ORGANISM: Homo Sapien

<400> SEQUENCE: 3

| caaggacatg gaatttcgga ccttctgtcc ccaccctctc tgctgagcct aggaaccctct | 60 |
| gagcagcagg aaggccttgg gtctagagcc tagaaatgga cccccacgtc cacctgccca | 120 |
| gcctagaccc ccagcattga agggtggtca gacttcctgt gagaggaagc cactaagcgg | 180 |
| gatggacacc atcgcccact ccacccggcc ctgcccagcc ctgcccagtc cagcccagtc | 240 |
| cagcccagcc ctgcccttcc cagccctgcc cagcccagct catccctgcc ctacccagcc | 300 |
| cagccctgtc ctgccctgcc cagcccagcc cagcccagcc ctgccctgcc ctgccctgcc | 360 |
| cttcccagcc ctgaccttcc cagccctgcc cagcccagct catccctgcc ctacccagct | 420 |
| cagccctgcc ctgccctgcc ctgccctgcc cagccctacc cagcccagcc ctgccctgcc | 480 |
| ctgcccagct cagccctgcc caccccagcc cagcccagcc cagcatgcgt tctctggatg | 540 |
| gtgagcacag gcttgacctt agaaagaggc tggcaacgag ggctgaggcc accaggccac | 600 |
| tgggtgctca cgggtcagac aagcccagag cctgctcccc tgccacgggt cggggctgtc | 660 |
| accgccagca tgctgtggat gtgcatggcc tcagggctgc tggctccagg ctgccccgc | 720 |
| cctggctccc gaggccaccc ctcttatgcc atgaaccctg tgccacaccc acctctgagc | 780 |
| tgtccccgct cctgccgcct gcaccccctg agcagcccc tgtgtgtttc atgggagtct | 840 |
| tagcaaggaa ggggagctcg aattcctgca gcccggg | 877 |

<210> SEQ ID NO 4
<211> LENGTH: 1960
<212> TYPE: DNA
<213> ORGANISM: Homo Sapien
<220> FEATURE:
<221> NAME/KEY: variation
<222> LOCATION: (1016)...(1016)
<223> OTHER INFORMATION: a, t, g or c
<221> NAME/KEY: variation
<222> LOCATION: (1126)...(1126)
<223> OTHER INFORMATION: a, t, g or c

<400> SEQUENCE: 4

| ccgggtaccg agctcccagg aagataaatg atttcctcct ctctagagat gggggtggga | 60 |
| tctgagcact cagagccaag ggcgcagtgg gtccgggcgg gggccctcct cggccctccc | 120 |
| aacatggggg ccaggaggtc agcccctcaa cctggacccc ggctgggtct cagggaatgg | 180 |
| tctcccccag tggcccagct tgcttgtgtt ttcagatggg tgtgcatggg tgtgtgtgtg | 240 |
| tgtgtgtgtg tgtgtgtgtg tgtgtgtgtg tgtgatgcct gacaagcccc agagagccaa | 300 |
| agacctgagt ggagatcttg tgacttctca aaaggggggat tggaaggttc gagaaagagc | 360 |
| tgtggtcagc cttgctctcc cttaaggctg tggtaaccac actaggcata gcataggcct | 420 |
| gcgcccccgtc cctccttccc tcctccgcgc ctctccttc tctttctccc cctctaccc | 480 |
| cgctccctgg cctgctcctg gtgacaccgt tggcccccctt ccagggctga gggaagccag | 540 |
| cgggggcccc ttcctgaaag cccacctgca ggccggcttg ctgggaaggg gctgctctcg | 600 |
| cagaggctcc cgcccgccct gcagccgttt cctggaagca gtcgctgtgg gtattctgtt | 660 |
| ccttgtcagc actgtgcttg caaagaaagc agacactgtg ctccttgtcc ttagggagcc | 720 |
| ccgctccatc acccaacacc tggctggaca caggcggag gccgggtccg cggggagcgg | 780 |
| cgcggggctg gggccggacc attaaacaca cacgggcgcc aggcactgca ggctcctcct | 840 |

-continued

```
cctcctcctg cccagcgcct ctgctcacag gcacgtgcca agcccctagg ccaggaggcc      900
agcagtgggt gcagaacaag ctcctgggaa ggggtgcag gcggacccc cggggagaag        960 ggctggcagg gctgtggggg acgctgaccg tgggccccac gttgcagaaa actggntgcc     1020
tggctggaag atgggggaga tgccaagcct ctgaggcagc acgagcaggg tgcatggagg     1080
ccggggcgcg gggaggctgc actgcagcat gcaccccaaa gcccanaggg agtggagacc     1140
aggccctgga atcgagaagt agaaaggcgg cttggaggcc tcggaaccgg ctgacctcca     1200
acagagtggg tctccagcct ggctctgccc tgccgcaggt cccctcccct cattaccagg     1260
cctagagcct ccagtcccgg tggcccccag cccgagggtg aacggcctca ccctgggtcg     1320
tgggacagag ggcacgttca tcaagagtgg ctcccaaggg acacgtggct gtttgcagtt     1380
cacaggaagc attcgagata aggagcttgt tttcccagtg ggcacggagc cagcaggggg     1440
gctgtggggc agcccagggt gcaaggccag gctgtggggc tgcagctgcc ttgggcccca     1500
ctcccaggcc tttgcgggag gtgggaggcg ggaggcggca gctgcacagt ggccccaggc     1560
gaggctctca gccccagtcg ctctccgggt gggcagccca agagggtctg gctgagcctc     1620
ccacatctgg gactccatca cccaacaact taattaaggc tgaatttcac gtgtcctgtg     1680
acttgggtag acaaagcccc tgtccaaagg ggcagccagc ctaaggcagt ggggacggcg     1740
tgggtggcgg gcgacggggg agatggacaa caggaccgag ggtgtgcggg cgatggggga     1800
gatggacaac aggaccgagg gtgtgcgggc gatgggggag atggacaaca ggaccgaggg     1860
tgtgcgggac acgcatgtca ctcatgcacg ccaatggggg gcgtgggagg ctggggagca     1920
gacagactgg gctgggctgg gcgggaagga cgggcagatg                           1960
```

<210> SEQ ID NO 5
<211> LENGTH: 4085
<212> TYPE: DNA
<213> ORGANISM: Homo Sapien
<220> FEATURE:
<221> NAME/KEY: variation
<222> LOCATION: (1016)...(1016)
<223> OTHER INFORMATION: a, t, c or g
<221> NAME/KEY: variation
<222> LOCATION: (1126)...(1126)
<223> OTHER INFORMATION: a, t, c or g
<221> NAME/KEY: variation
<222> LOCATION: (2194)...(2194)
<223> OTHER INFORMATION: a, t, c or g
<221> NAME/KEY: variation
<222> LOCATION: (3235)...(3235)
<223> OTHER INFORMATION: a, t, c or g

<400> SEQUENCE: 5

```
ccgggtaccg agctcccagg aagataaatg atttcctcct ctctagagat ggggtggga       60 tctgagcact cagagccaag ggcgcagtgg gtccgggcgg gggccctcct cggccctccc     120
aacatggggg ccaggaggtc agcccctcaa cctggacccc ggctgggtct cagggaatgg     180
tctcccccag tggcccagct tgcttgtgtt ttcagatggg tgtgcatggg tgtgtgtgtg     240
tgtgtgtgtg tgtgtgtgtg tgtgtgtgtg tgtgatgcct gacaagcccc agagagccaa     300
agacctgagt ggagatcttg tgacttctca aaagggggat tggaaggttc gagaaagagc     360
tgtggtcagc cttgctctcc cttaaggctg tggtaaccac actaggcata gcataggcct     420
gcgccccgtc cctccttccc tcctccgcgc ctctcctttc tctttctccc ccctctaccc     480
cgctccctgg cctgctcctg gtgacaccgt tggcccccctt ccaggctga gggaagccag     540 cgggggcccc ttcctgaaag cccacctgca ggccggcttg ctgggaaggg gctgctctcg     600
```

| | |
|---|---|
| cagaggctcc cgcccgccct gcagccgttt cctggaagca gtcgctgtgg gtattctgtt | 660 |
| ccttgtcagc actgtgcttg caaagaaagc agacactgtg ctccttgtcc ttagggagcc | 720 |
| ccgctccatc acccaacacc tggctggaca caggcgggag gccgggtccg cggggagcgg | 780 |
| cgcggggctg gggccggacc attaaacaca cacgggcgcc aggcactgca ggctcctcct | 840 |
| cctcctcctg cccagcgcct ctgctcacag gcacgtgcca agccctagg ccaggaggcc | 900 |
| agcagtgggt gcagaacaag ctcctgggaa ggggtgcag gcggacccc ggggagaag | 960 |
| ggctggcagg gctgtggggg acgctgaccg tgggccccac gttgcagaaa actggntgcc | 1020 |
| tggctggaag atgggggaga tgccaagcct ctgaggcagc acgagcaggg tgcatggagg | 1080 |
| ccggggcgcg gggaggctgc actgcagcat gcaccccaaa gcccanaggg agtggagacc | 1140 |
| aggccctgga atcgagaagt agaaaggcgg cttggaggcc tcggaaccgg ctgacctcca | 1200 |
| acagagtggg gccggccctg gaggcaaaga ggtgcccggg gtccggccct gcctggggga | 1260 |
| gctatgtgtc atgggcaagc acaggatat gtagcccgct ctgagcctat ggacccaggg | 1320 |
| cagggctgca aggcagggca ggggagacag cacgggggag caaggagcag agaggggcc | 1380 |
| tcaggctctc ccaggaggaa cattctcccg acaggaggaa gagacggccc agggtgact | 1440 |
| gtggggagcc atggtggcag ctgggtcgt ggcagatggg agagaggctg gcgaggtgaa | 1500 |
| ggtgcagggg tcagggctct ggggcccaca tgcctgtggg agcaggcagg cccagggctc | 1560 |
| tccgccactc cccactcccg cttggctcat aggctgggcc caagggtggg gtgggatgag | 1620 |
| caggagatgg ggcccagggg gcaagcaggg ccccaaagac atttagaaaa accggttttat | 1680 |
| gcaggcagca ttcagagcag gcggcgtgcg tggcggggc cctgggagca cagagaggca | 1740 |
| cacgtagggc ccccgagggg ctccccattg gccggcagta acatcacccc tgtgtcaaca | 1800 |
| gtgatgtctg cagctccggc cagccagggt ttatggagcg agaccagcc cggcctgggc | 1860 |
| cctcactccc caggcccaca cactagccca ctgttcaggg tccggggtgg cggcatggcc | 1920 |
| tgggggtcct ggcaccgctg ctcctctgcc caccctaact tccggcatc gcggctgccc | 1980 |
| cctctgagcc tccccaacca gtaagtgtgg ggccagcag gctgccgtc ctcctcctct | 2040 |
| tcccctctag agagaaacgt ggaggtcctg gggctggggg cgctcatagc cctgtgacac | 2100 |
| aggtgcatgg ggtcagggt cccagaatgg ccctgggaa ggacctcagc tgggccggcg | 2160 |
| gctctaggct tcagggtct gtctgcacag gggntagccc ctcccagacc tctgtgaagc | 2220 |
| cagtacgggc ctccctccc tgccccgtgc tctgtccggt gcttcctgga ctgcactgcg | 2280 |
| ggccactggt gagagggtgg acagggaagg gccgccgtgg tgcctgttcc tgcccacctg | 2340 |
| gctgtgtggt cccctccaag tagggacaac ccttctgagg gcttgggggc accctggggt | 2400 |
| tgccagggcc tcccagagcc ctgtgagccc ctgggggtc tggcctgatg cccccctcca | 2460 |
| cgtccagggc cggctgtggc ccagaacccc agcttcccag caggccggtg tgcggtggtg | 2520 |
| acccaggaga ggcctcgcct ccactgaggg gccaccgacc tctgtcagac cacagagacc | 2580 |
| cccaaggagt ctgaaggctg gagacccggg gctgggacca ggtgggactt tcccacggag | 2640 |
| ccgtccccag gccagctgg ggacacgtcc cccttctctc cagacacacc ctgcctgcca | 2700 |
| ccaggacaca ccgcctgtt gggggtctct tttaagtgct tgccactctg aggtgactgt | 2760 |
| ccctttccaa agaggtttct ggggcccagg tgggatgcgt cggcctgagc aggaggatct | 2820 |
| gggccgccag gggctgggga ctgtctcctg ggaaggaag cgcctgggag cgtgtgtgct | 2880 |
| gacccaggac catccaggga ggcccgtctg tgggcaagc gggaagggag cggctggaga | 2940 |
| ggcttggccg ccccgcccct gcctcccatt ccttagctcc atgcctgtca acctctgtca | 3000 |

-continued

```
cccagtgagt gatgtccagg ggccctggaa aggtcacagc atgtttgagc ggggtgagag      3060 agagggaaa ggcgggggcg gggaaaagta cgtggaggaa gctttaggcc caaggaagga       3120 gacaggttc tgggagggag ggagccactg gggccgccgg gaaggtccct gcttgctgct       3180
gccacccaga accctcgcct cttagctagc ccccgcagcc ccagccttc tggcntgtgg       3240 ccctctcccc catccccagg tgtcctgtgc aaccaggcct tggacccaaa ccctcctgcc      3300
ccctcctctc cctcctcacc ctcccaatgc agtggtctcc agcctggctc tgccctgccg      3360
caggtcccct cccctcatta ccaggcctag agcctccagt cccggtggcc cccagcccga      3420
gggtgaacgg cctcaccctg ggtcgtggga cagagggcac gttcatcaag agtggctccc      3480
aagggacacg tggctgtttg cagttcacag gaagcattcg agataaggag cttgttttcc      3540
cagtgggcac ggagccagca ggggggctgt ggggcagccc agggtgcaag gccaggctgt      3600
ggggctgcag ctgccttggg ccccactccc aggcctttgc gggaggtggg aggcgggagg      3660
cggcagctgc acagtggccc caggcgaggc tctcagcccc agtcgctctc cgggtgggca      3720
gcccaagagg gtctggctga gcctcccaca tctgggactc catcacccaa caacttaatt     3780
aaggctgaat ttcacgtgtc ctgtgacttg ggtagacaaa gccctgtcc aaaggggcag       3840 ccagcctaag gcagtgggga cggcgtgggt ggcgggcgac ggggagatg gacaacagga       3900 ccgagggtgt gcgggcgatg ggggagatgg acaacaggac cgagggtgtg cgggcgatgg      3960
gggagatgga caacaggacc gagggtgtgc gggacacgca tgtcactcat gcacgccaat     4020
ggggggcgtg ggaggctggg gagcagacag actgggctgg gctgggcggg aaggacgggc     4080
agatg                                                                 4085
```

<210> SEQ ID NO 6
<211> LENGTH: 22
<212> TYPE: DNA
<213> ORGANISM: Homo Sapien

<400> SEQUENCE: 6

```
cggttcccca cttccccagt tt                                              22
```

<210> SEQ ID NO 7
<211> LENGTH: 33
<212> TYPE: DNA
<213> ORGANISM: Homo Sapien

<400> SEQUENCE: 7

```
cggaagtcga caaccctcac caaaggccaa ggt                                  33
```

<210> SEQ ID NO 8
<211> LENGTH: 27
<212> TYPE: DNA
<213> ORGANISM: Homo Sapien

<400> SEQUENCE: 8

```
atatggtacc gacaaccctc accaaag                                         27
```

<210> SEQ ID NO 9
<211> LENGTH: 29
<212> TYPE: DNA
<213> ORGANISM: Homo Sapien

<400> SEQUENCE: 9

```
atataagctt cttctccctc accctgctc                                       29
```

```
<210> SEQ ID NO 10
<211> LENGTH: 23
<212> TYPE: DNA
<213> ORGANISM: Homo Sapien

<400> SEQUENCE: 10
acaggtacct ctagagtcga cct                                              23

<210> SEQ ID NO 11
<211> LENGTH: 24
<212> TYPE: DNA
<213> ORGANISM: Homo Sapien

<400> SEQUENCE: 11
atataagctt gctcccatcc tgca                                             24
```